(12) United States Patent
Gougeon et al.

(10) Patent No.: US 10,018,629 B2
(45) Date of Patent: Jul. 10, 2018

(54) CORRELATION OF DISEASE ACTIVITY WITH CLONAL EXPANSIONS OF HUMAN PAPILLOMAVIRUS 16-SPECIFIC CD8+ T-CELLS IN PATIENTS WITH SEVERE EROSIVE ORAL LICHEN PLANUS

(71) Applicants: INSTITUT PASTEUR, Paris (FR); INSTITUT NATIONAL DE LA SANTE ET DE LA RECHERCHE MEDICALE (INSERM), Paris (FR); UNIVERSITE PARIS DIDEROT PARIS 7, Paris (FR); ASSISTANCE PUBLIQUE—HOPITAUX DE PARIS, Paris (FR)

(72) Inventors: Marie-Lise Gougeon, Antony (FR); Manuelle Viguier, Paris (FR); Hervé Bachelez, Paris (FR); Nicolas Fazilleau, La Salvetat Saint Gilles (FR)

(73) Assignees: INSTITUTE PASTEUR, Paris (FR); INSTITUT NATIONAL DE LA SANTE ET DE LA RECHERCHE MEDICALE (INSERM), Paris (FR); UNIVERSITE PARIS DIDEROT-PARIS 7, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 14/910,612

(22) PCT Filed: Aug. 8, 2014

(86) PCT No.: PCT/EP2014/067131
§ 371 (c)(1),
(2) Date: Feb. 5, 2016

(87) PCT Pub. No.: WO2015/018943
PCT Pub. Date: Feb. 12, 2015

(65) Prior Publication Data
US 2016/0195531 A1    Jul. 7, 2016

Related U.S. Application Data

(60) Provisional application No. 61/863,453, filed on Aug. 8, 2013.

(51) Int. Cl.
| | | |
|---|---|---|
| *C07K 14/025* | (2006.01) | |
| *G01N 33/569* | (2006.01) | |
| *A61K 39/12* | (2006.01) | |
| *C07K 14/005* | (2006.01) | |
| *C07K 14/235* | (2006.01) | |
| *C12N 7/00* | (2006.01) | |
| *C12Q 1/04* | (2006.01) | |
| *C12Q 1/6869* | (2018.01) | |
| *A61K 31/675* | (2006.01) | |
| *A61K 39/02* | (2006.01) | |
| *A61K 45/06* | (2006.01) | |
| *A61N 5/06* | (2006.01) | |

(Continued)

(52) U.S. Cl.
CPC ..... *G01N 33/56983* (2013.01); *A61K 31/675* (2013.01); *A61K 39/099* (2013.01); *A61K 39/12* (2013.01); *A61K 45/06* (2013.01); *A61N 5/0613* (2013.01); *C07K 14/005* (2013.01); *C07K 14/235* (2013.01); *C12N 7/00* (2013.01); *C12Q 1/04* (2013.01); *C12Q 1/6869* (2013.01); *C12Q 1/708* (2013.01); *G01N 33/502* (2013.01); *G01N 33/56972* (2013.01); *A61K 2039/545* (2013.01); *A61K 2039/572* (2013.01); *A61K 2039/575* (2013.01); *C07K 2319/55* (2013.01); *C12N 2710/20034* (2013.01); *C12Q 2600/158* (2013.01); *G01N 33/505* (2013.01); *G01N 33/5008* (2013.01); *G01N 33/5091* (2013.01); *G01N 2333/025* (2013.01); *G01N 2333/7051* (2013.01); *G01N 2800/18* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |

(Continued)

FOREIGN PATENT DOCUMENTS

| | | |
|---|---|---|
| WO | WO88/10315 A1 | 12/1988 |
| WO | WO90/06995 A1 | 6/1990 |

(Continued)

OTHER PUBLICATIONS

Mattila et al. Human papillomavirus in oral atrophic lichen planus lesions. Oral Oncology 48 (2012) 980-984.*

(Continued)

*Primary Examiner* — Nianxiang Zou
(74) *Attorney, Agent, or Firm* — Arrigo, Lee, Guttmann & Mouta-Bellum LLP

(57) ABSTRACT

A massive clonal expansion of activated CD8+ T-cells with increased frequency of HPV 16-specific CD8+ T-cells was discovered to be a characteristic of oral lichen planus (OLP), indicating a causal link between HPV infection and the dysimmune process. The invention relates to compositions and methods for the diagnosis and treatment of OLP patients.

9 Claims, 9 Drawing Sheets

(51) Int. Cl.
*C12Q 1/70* (2006.01)
*G01N 33/50* (2006.01)
*A61K 39/00* (2006.01)

(56) References Cited

U.S. PATENT DOCUMENTS

| | | |
|---|---|---|
| 4,800,159 A | 1/1989 | Mullis et al. |
| 4,965,188 A | 10/1990 | Mullis et al. |
| 4,988,617 A | 1/1991 | Landegren et al. |
| 5,130,238 A | 7/1992 | Malek et al. |
| 5,242,794 A | 9/1993 | Whiteley et al. |
| 5,333,675 A | 8/1994 | Mullis et al. |
| 5,409,818 A | 4/1995 | Davey et al. |
| 5,494,810 A | 2/1996 | Barany et al. |
| 5,554,517 A | 9/1996 | Davey et al. |
| 6,063,603 A | 5/2000 | Davey et al. |
| 6,410,276 B1 | 6/2002 | Burg et al. |
| 6,582,938 B1 | 6/2003 | Su et al. |
| 9,547,006 B2 | 1/2017 | Gougeon et al. |

FOREIGN PATENT DOCUMENTS

| | | |
|---|---|---|
| WO | WO03/093496 A1 | 11/2003 |
| WO | WO2005/089792 A1 | 9/2005 |
| WO | WO2008/116078 A2 | 9/2008 |
| WO | WO2008/147187 A1 | 12/2008 |
| WO | WO2011/088573 A1 | 7/2011 |

OTHER PUBLICATIONS

Gotoh et al. Skew in T cell receptor usage with polyclonal expansion in lesions of oral lichen planus without hepatitis C virus infection. Clin Exp Immunol. Nov. 2008;154(2):192-201. Epub Sep. 8, 2008.*

Sirianni et al. Antiviral activity of Cidofovir on a naturally human papillomavirus-16 infected squamous cell carcinoma of the head and neck (SCCHN) cell line improves radiation sensitivity. Oral Oncology (2005) 41, 423-428.*

Pilch et al. Improved Assessment of T-Cell Receptor (TCR) VB Repertoire in Clinical Specimens: Combination of TCR-CDR3 Spectratyping with Flow Cytometry-Based TCR VB Frequency Analysis Clin Diagn Lab Immunol. Mar. 2002; 9(2): 257-266.*

Gorsky et al. Oral lichen planus: malignant transformation and human papilloma virus: A review of potential clinical implications. Oral Surg Oral Med Oral Pathol Oral Radiol Endod 2011;111:461-464.*

Kanodia et al. Recent advances in strategies for immunotherapy of human papillomavirus-induced lesions. Int. J. Cancer: 122, 247-259 (2008).*

Campisi et al. Controversies surrounding human papilloma virus infection, head & neck vs oral cancer, implications for prophylaxis and treatment. Head & Neck Oncology 2009, 1:8.

Simen-Kapeu et al. Lack of association between human papillomavirus type 16 and 18 infections and female lung cancer. Cancer Epidemiol Biomarkers Prev. Jul. 2010;19(7):1879-81. Epub Jun. 15, 2010.

Nilges et al., Human Papillomavirus Type 16 E7 Peptide-Directed CD8+ T Cells from Patients with Cervical Cancer Are Cross-Reactive with the Coronavirus NS2 Protein. Journal of Virology, 2003, 77:5464-5474.

Viguier et al., Effector and regulatory T cell populations in patients treated with extracorporeal photochemotherapy for severe erosive Lichen planus, Database Biosis accession No. PREV200600059533, Biosciences Information Service, Philadelphia, PA, US; Sep. 2005 (Sep. 2005).

Viguier et al., Peripheral and Local Human Papillomavirus 16-Specific CD8+ T-Cell Expansions Characterize Erosive Oral Lichen Planus, J Invest Dermatol. Sep. 2014; ISSN: 0022-202X.

Farhi et al., Pathophysiology, etiologic factors, and clinical management of oral lichen planus, part I: facts and controversies, Clin Dermatol. Jan. 2010 ;28(1):100-8.

Lodi G, Scully C, Carrozzo M, Griffiths M, Sugerman PB, Thongprasom K. Current controversies in oral lichen planus: report of an international consensus meeting. Part 2. Clinical management and malignant transformation. Oral Surg Oral Med Oral Pathol Oral Radiol Endod 2005; 100:164-178.

Lodi G, Scully C, Carrozzo M, Griffiths M, Sugerman PB, Thongprasom K. Current controversies in oral lichen planus: report of an international consensus meeting. Part 1. Viral infections and etiopathogenesis. Oral Surg Oral Med Oral Pathol Oral Radiol Endod 2005; 100:40-51.

Cox et al., Human herpes simplex-1 and papillomavirus type 16 homologous DNA sequences in normal, potentially malignant and malignant oral mucosa, Eur J Cancer B Oral Oncol. Jul. 1993;29B(3):215-9.

Campisi et al., HPV DNA in clinically different variants of oral leukoplakia and lichen planus, Oral Surg Oral Med Oral Pathol Oral Radiol Endod. Dec. 2004;98(6):705-11.

Benay Tokman, Burcu Senguven, PP4-179—Prevalence of EBV, HPV 16 and HSV-1 in oral lichen planus, Virchows Archiv, Springer, Berlin. Aug. 2007;451(2):549-549.

Alvarez et al., Am J Transplant. Apr. 2005;5 (4 Pt 1):746-56.

Hoffmann et al., Int. J. Cancer: 118, 1984-1991 (2006).

Barrios et al., Cancer Immunol Immunother. Aug. 2012, 61(8):1307-17.

Becherel PA, Bussel A, Chosidow O, Rabian C, Piette JC, Frances C. Extracorporeal photochemotherapy for chronic erosive lichen planus. Lancet 1998;351:805.

Blattman et al., The Journal of Immunology Dec. 1, 2000 vol. 165 No. 11 6081-6090.

Combita AL, Bravo MM, Touze A, Orozco O, Coursaget P. Serologic response to human oncogenic papillomavirus types 16, 18, 31, 33, 39, 58 and 59 virus-like particles in colombian women with invasive cervical cancer. Int J Cancer 2002;97:796-803.

Yildirim B, Senguven B, Demir C. Prevalence of herpes simplex, Epstein Barr and human papilloma viruses in oral lichen planus. Medicina oral, patologia oral y cirugia bucal 2011;16:e170-4.

Edwards PC, Kelsch R. Oral lichen planus: clinical presentation and management. J Can Dent Assoc 2002;68:494-9.

Guatelli et al., Proc. Nat. Acad. Sci. USA, 87, 1874 (1990).

Guyot AD, Farhi D, Ingen-Housz-Oro S, et al. Treatment of refractory erosive oral lichen planus with extracorporeal photochemotherapy: 12 cases.The British journal of dermatology 2007;156:553-6.

Huang et al., Antiviral Res. Feb. 2012, 93(2): 280-287.

Hung et al., Expert Opin Biol Ther. Apr. 2008; 8(4): 421-439.

Jontell M, Watts S, Wallstrom M, Levin L, Sloberg K. Human papilloma virus in erosive oral lichen planus. J Oral Pathol Med 1990; 19:273-7.

Knechtle, Phil. Trans. R. Soc. Lond (2001) 356, 681-689.

Zhou XJ, Sugerman PB, Savage NW, Walsh LJ, Seymour GJ. Intra-epithelial CD8+ T cells and basement membrane disruption in oral lichen planus. J Oral Pathol Med 2002;31:23-7.

Le Cleach L, Chosidow O. Clinical practice. Lichen planus. N Engl J Med 2012;366:723-32.

Lecoeur, Melki, Saïdi, Gougeon. Methods Enzymol. 2008;442:51-82.

Li et al., Oncology Reports 24: 1323-1329, 2010.

Lim et al., J Immunol Methods. Mar. 1, 2002;261(1-2):177-94.

Lin et al., Immunol Res. Jul. 2010, 47(1-3): 86-112.

Zentz et al., Human Immunology 68,75-85 (2007).

Miller CS, White DK, Royse DD. In situ hybridization analysis of human papillomavirus in orofacial lesions using a consensus biotinylated probe. Am J Dermatopathol 1993; 15:256-9.

Natale C, Giannini T, Lucchese A, Kanduc D. Computer-assisted analysis of molecular mimicry between human papillomavirus 16 E7 oncoprotein and human protein sequences. Immunol Cell Biol 2000;78:580-5.

Nico et al., An Bras Dermatol. 2011;86(4):633-43.

Preville et al., Cancer Res 2005;65:641-649.

(56) References Cited

OTHER PUBLICATIONS

Santoro A, Majorana A, Bardellini E, et al. Cytotoxic molecule expression and epithelial cell apoptosis in oral and cutaneous lichen planus. Am J Clin Pathol 2004;121:758-64.
Selmi C, Leung PS, Sherr DH, et al Mechanisms of environmental influence on human autoimmunity: a National Institute of Environmental Health Sciences expert panel workshop. J Autoimmun 2012;39:272-84.
Sugerman PB, Satterwhite K, Bigby M. Autocytotoxic T-cell clones in lichen planus. The British journal of dermatology 2000;142:449-56.
Zanotto et al. Journal of Translational Medicine 2011, 9:190.
Wang et al., Clinical and Vaccine Immunology, vol. 15, No. 6, Jun. 2008, p. 937-945.
White et al., J. Biol. Chem. 2003, 278:26765-26772.
Young SK, Min KW. In situ DNA hybridization analysis of oral papillomas, leukoplakias, and carcinomas for human papillomavirus. Oral surgery, oral medicine, and oral pathology 1991;71:726-9.

\* cited by examiner

Supplementary Table 1. Characteristics of the studied patients

| Patients | Gender/Age at inclusion | Lichen localizations/duration | Treatment received before ECP | Best response to ECP | HLA class I typing |
|---|---|---|---|---|---|
| OLP1* | F/40 y. | Buccal/2 y. | Topical ciclosporin | CR | A*03/A*32<br>B*40/B*5001<br>CW*03/CW*06 |
| OLP2 | F/53 y. | Buccal, genital, skin/23 y. | Topical steroids, topical ciclosporin, systemic ciclosporin, efalizumab, MTX | CR | A*02<br>B*35<br>CW*04 |
| OLP3* | F/78 y. | Buccal, genital/5 y. | Topical tretinoin | PR | A*02/A*68<br>B*14/B*58<br>CW*03/CW*08 |
| OLP4* | F/74 y. | Buccal, genital, skin/12 y. | CS, AZA, topical ciclosporin | PR | A*02/A*68<br>B*08/B*14<br>CW*07/CW*08 |
| OLP5* | F/47 y. | Buccal, genital, skin/3 y. | None | PR | A*11/A*68<br>B*15/B*35<br>CW*04/CW*07 |
| OLP6* | F/54 y. | Buccal, genital/1 y | Topical ciclosporin, topical tretinoin | CR | A*02/A*30<br>B*13/B*18<br>CW*05/CW*06 |
| OLP7* | M/74 y. | Buccal/5 y. | CS, topical tretinoin | CR | A*02<br>B*44/B*57<br>CW*05/CW*06 |
| OLP8 | M/25 y. | Buccal, genital/9 y. | Topical steroids, topical ciclosporin, systemic steroids, acitretin | PR | A*33<br>B*14/B*58<br>CW*03/CW*08 |
| OLP9* | F/60 y. | Buccal, genital, skin/14 y | CS, AZA, acitretin | CR | A*11/A*24<br>B*15/B*35<br>CW*04/CW*07 |
| OLP10* | F/60 y. | Buccal, genital, skin/5 y. | Topical ciclosporin | CR | A*01/A*11<br>B*08/B*35<br>CW*04/CW*07 |

Abbreviations used : AZA: azathioprine ; CR: complete remission; CS: corticosteroids; ECP : extracorporeal photochemotherapy, F : female ; M : male; MTX : methotrexate ; PR: partial remission ; y: years.
*These patients have been previously reported elsewhere[3].

Cytotoxic granules expression in peripheral expanded CTL from OLP Patients

| Marker expression/subset | Pt BRE | Pt WO | Pt EL | Pt GR |
|---|---|---|---|---|
| CD8+Vβ3+/CD8+ | 5,95 | 25,33 | 14,88 | 15,68 |
| HPV+/CD8+ | 8,9 | 5,36 | 5,07 | 4,8 |
| Perforin/CD8+ | 8,30 | 0,17 | 21,70 | 9,93 |
| Perforin/CD8+Vβ3+ | 9,90 | 0,19 | 14,60 | 12,03 |
| Perforin/CD8+HPV+ | 3,17 | 0,13 | 7,22 | 11,40 |
| Perforin/CD8+Vβ3+HPV+ | 1,67 | 0,14 | 10,90 | 8,00 |
| Granzyme/CD8+ | 35,20 | 29,23 | 56,80 | 39,33 |
| Granzyme/CD8+Vβ3+ | 26,50 | 26,25 | 75,40 | 45,60 |
| Granzyme/CD8+HPV+ | 27,15 | 10,70 | 57,00 | 39,60 |
| Granzyme/CD8+Vβ3+HPV+ | 17,60 | 17,20 | 37,90 | 31,20 |

SEQUENCE LISTING

<160> NUMBER OF SEQ ID NOS: 30

<210> SEQ ID NO 1
<211> LENGTH: 11
<212> TYPE: PRT

-continued

```
<213> ORGANISM: artificial
<220> FEATURE:
<223> OTHER INFORMATION: CDR3 beta sequence of the TCR V beta 3 gene
      segment in T cells

<400> SEQUENCE: 1

Ser Phe Val Ile Gly Gly Val Ser Asn Pro Gln
1               5                   10

<210> SEQ ID NO 2
<211> LENGTH: 10
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 2

Ser Glu Pro Gly Gln Gly Phe Gly Glu Gln
1               5                   10

<210> SEQ ID NO 3
<211> LENGTH: 8
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 3

Ser Ile Gly Leu His Tyr Glu Gln
1               5

<210> SEQ ID NO 4
<211> LENGTH: 8
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 4

Ser Leu Gly Val His Tyr Glu Gln
1               5

<210> SEQ ID NO 5
<211> LENGTH: 11
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 5

Ser Gln Gly Val Phe Leu Gly Ala Gly Glu Leu
1               5                   10

<210> SEQ ID NO 6
<211> LENGTH: 12
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 6

Ser Leu Leu Glu Gly Leu Ala Gly Val Asp Glu Gln
1               5                   10
```

```
<210> SEQ ID NO 7
<211> LENGTH: 13
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 7

Ser Tyr Ile Gly Leu Gln Ser Lys Ala Asn Tyr Gly Tyr
1               5                   10

<210> SEQ ID NO 8
<211> LENGTH: 10
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 8

Ser Glu Pro Gly Gln Gly Phe Gly Glu Gln
1               5                   10

<210> SEQ ID NO 9
<211> LENGTH: 7
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 9

Ser Phe Gln Pro Gly Gly Gln
1               5

<210> SEQ ID NO 10
<211> LENGTH: 7
<212> TYPE: PRT
<213> ORGANISM: artificial
<220> FEATURE:
<223> OTHER INFORMATION: CDR3 beta sequence of the TCR V beta 3 gene
      segment in T cells

<400> SEQUENCE: 10

Ser Leu Thr Thr Gly Glu Leu
1               5

<210> SEQ ID NO 11
<211> LENGTH: 45
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 11
tgtgccagca gttttgtcat tgggggggtt agcaatcagc cccag                    45

<210> SEQ ID NO 12
<211> LENGTH: 39
<212> TYPE: DNA
<213> ORGANISM: artificial
<220> FEATURE:
<223> OTHER INFORMATION: CDR3 beta sequence of the TCR V beta 3 gene
      segment in T cells
```

<400> SEQUENCE: 12
tgtgccagca gtgaaccggg acagggtttt ggtgagcag                              39

<210> SEQ ID NO 13
<211> LENGTH: 33
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 13
tgtgccagca gtatagggct ccactacgag cag                                    33

<210> SEQ ID NO 14
<211> LENGTH: 33
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 14
tgtgccagca gtttaggtgt gcactacgag cag                                    33

<210> SEQ ID NO 15
<211> LENGTH: 42
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 15
tgtgccagca gtcaaggagt cttcctgggg gccggggagc tg                          42

<210> SEQ ID NO 16
<211> LENGTH: 45
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 16
tgtgccagca gtttattgga gggactagcg ggagtggatg agcag                       45

<210> SEQ ID NO 17
<211> LENGTH: 48
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 17
tgtgccagca gttatatagg cctacagagt aaagctaact atggctac                    48

<210> SEQ ID NO 18
<211> LENGTH: 39
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 18

```
tgtgccagca gtgaaccggg acagggtttt ggtgagcag                          39
```

<210> SEQ ID NO 19
<211> LENGTH: 30
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 19

```
tgtgccagca gtttccaacc aggggggcag                                    30
```

<210> SEQ ID NO 20
<211> LENGTH: 30
<212> TYPE: DNA
<213> ORGANISM: artificial
<220> FEATURE:
<223> OTHER INFORMATION: CDR3 beta sequence of the TCR V beta 3 gene
      segment in T cells

<400> SEQUENCE: 20

```
tgtgccagca gtttaaccac cggggagctg                                    30
```

<210> SEQ ID NO 21
<211> LENGTH: 9
<212> TYPE: PRT
<213> ORGANISM: artificial
<220> FEATURE:
<223> OTHER INFORMATION: HPV peptide

<400> SEQUENCE: 21

His Tyr Asn Ile Val Thr Phe Cys Cys
1               5

<210> SEQ ID NO 22
<211> LENGTH: 9
<212> TYPE: PRT
<213> ORGANISM: artificial
<220> FEATURE:
<223> OTHER INFORMATION: HPV peptide

<400> SEQUENCE: 22

Lys Leu Cys Leu Arg Phe Leu Ser Lys
1               5

<210> SEQ ID NO 23
<211> LENGTH: 9
<212> TYPE: PRT
<213> ORGANISM: artificial
<220> FEATURE:
<223> OTHER INFORMATION: HPV peptide

<400> SEQUENCE: 23

Lys Pro Thr Leu Lys Glu Tyr Val Leu
1               5

<210> SEQ ID NO 24
<211> LENGTH: 10
<212> TYPE: PRT
<213> ORGANISM: artificial
<220> FEATURE:
<223> OTHER INFORMATION: HPV peptide

<400> SEQUENCE: 24

Leu Leu Met Gly Thr Leu Gly Ile Val Cys

<210> SEQ ID NO 25
<211> LENGTH: 9
<212> TYPE: PRT
<213> ORGANISM: artificial
<220> FEATURE:
<223> OTHER INFORMATION: HPV peptide

<400> SEQUENCE: 25

Met Leu Asp Leu Gln Pro Glu Thr Thr
1               5

<210> SEQ ID NO 26
<211> LENGTH: 9
<212> TYPE: PRT
<213> ORGANISM: artificial
<220> FEATURE:
<223> OTHER INFORMATION: HPV peptide

<400> SEQUENCE: 26

Asn Thr Leu Glu Gln Thr Val Lys Lys
1               5

<210> SEQ ID NO 27
<211> LENGTH: 9
<212> TYPE: PRT
<213> ORGANISM: artificial
<220> FEATURE:
<223> OTHER INFORMATION: HPV peptide

<400> SEQUENCE: 27

Arg Ala His Tyr Asn Ile Val Thr Phe
1               5

<210> SEQ ID NO 28
<211> LENGTH: 9
<212> TYPE: PRT
<213> ORGANISM: artificial
<220> FEATURE:
<223> OTHER INFORMATION: HPV peptide

<400> SEQUENCE: 28

Val Pro Thr Leu Gln Asp Val Val Leu
1               5

<210> SEQ ID NO 29
<211> LENGTH: 10
<212> TYPE: PRT
<213> ORGANISM: artificial
<220> FEATURE:
<223> OTHER INFORMATION: HPV peptide

<400> SEQUENCE: 29

Tyr Met Leu Asp Leu Gln Pro Glu Thr Thr
1               5                   10

<210> SEQ ID NO 30
<211> LENGTH: 35
<212> TYPE: PRT
<213> ORGANISM: artificial
<220> FEATURE:
<223> OTHER INFORMATION: HPV peptide E7 43-77

<400> SEQUENCE: 30

Gly Gln Ala Glu Pro Asp Arg Ala His Tyr Asn Ile Val Thr Phe Cys
1               5                   10                  15

```
Cys Lys Cys Asp Ser Thr Leu Arg Leu Cys Val Gln Ser Thr His Val
            20                  25                  30
Asp Ile Arg
        35
```

CORRELATION OF DISEASE ACTIVITY WITH CLONAL EXPANSIONS OF HUMAN PAPILLOMAVIRUS 16-SPECIFIC CD8+ T-CELLS IN PATIENTS WITH SEVERE EROSIVE ORAL LICHEN PLANUS

This application claims the benefit of priority to U.S. Provisional Patent Application No. 61/863,453, filed Aug. 8, 2013.

BACKGROUND OF THE INVENTION

Lichen planus is a chronic inflammatory disease of unknown etiology involving the skin and/or mucous membranes, leading to a variety of clinical presentations (Le Cleach L, Chosidow O. Clinical practice. Lichen planus. N Engl J Med 2012; 366:723-32). Oral lichen planus (OLP) is the most prevalent subtype in this latter entity, affecting 0.1 to 4% of the general population, and is characterized by a severely disabling course in its ulcerative form, which often require immunomodulatory systemic therapies such as oral steroids, immunosuppressants and more recently extracorporeal photochemotherapy (ECP)(Edwards P C, Kelsch R. Oral lichen planus: clinical presentation and management. J Can Dent Assoc 2002; 68:494-9; Guyot A D, Farhi D, Ingen-Housz-Oro S, et al. Treatment of refractory erosive oral lichen planus with extracorporeal photochemotherapy: 12 cases. The British journal of dermatology 2007; 156:553-6; Becherel P A, Bussel A, Chosidow O, Rabian C, Piette J C, Frances C. Extracorporeal photochemotherapy for chronic erosive lichen planus. Lancet 1998; 351:805).

OLP is a chronic, disabling muco-cutaneous dys-immune rare disease characterized by mucosal inflammatory erosive lesions with pathological evidence for a marked CD8+ cytotoxic T-cell (CTL) infiltration. Pathologically, OLP is characterized by a predominant infiltrate of immune cells, mainly CD8+ cytotoxic T-lymphocytes (CTLs), associated with apoptosis of epithelial cells and disruption of the basement membrane zone (Zhou X J, Sugerman P B, Savage N W, Walsh L J, Seymour G J. Intra-epithelial CD8+ T cells and basement membrane disruption in oral lichen planus. J Oral Pathol Med 2002; 31:23-7). Likewise, the presence in OLP lesions of activated CTLs in the vicinity of damaged epithelial cells, supports the hypothesis that a dys-regulated cytotoxic T-cell response of unknown antigen specificity plays a key role in the pathogenesis of the disease (Santoro A, Majorana A, Bardellini E, et al. Cytotoxic molecule expression and epithelial cell apoptosis in oral and cutaneous lichen planus. Am J Clin Pathol 2004; 121:758-64).

However, the nature of these antigens remains controversial. Indeed, while autoreactivity of lesional skin-derived CTLs against epithelial cells has been suggested by studies in OLP patients (Sugerman P B, Satterwhite K, Bigby M. Autocytotoxic T-cell clones in lichen planus. The British journal of dermatology 2000; 142:449-56), several studies identified the presence of DNA from several Human Papilloma Virus (HPV) subtypes including HPV16 and HPV18 in mucosal lesions of OLP, raising the issue of the self versus non-self (HPV) nature of target antigens in OLP, two non-mutually exclusive hypotheses (Jontell M, Watts S, Wallstrom M, Levin L, Sloberg K. Human papilloma virus in erosive oral lichen planus. J Oral Pathol Med 1990; 19:273-7; Young S K, Min K W. In situ DNA hybridization analysis of oral papillomas, leukoplakias, and carcinomas for human papillomavirus. Oral surgery, oral medicine, and oral pathology 1991; 71:726-9; Lodi G, Scully C, Carrozzo M, Griffiths M, Sugerman P B, Thongprasom K. Current controversies in oral lichen planus: report of an international consensus meeting. Part 1. Viral infections and etiopathogenesis. Oral Surg Oral Med Oral Pathol Oral Radiol Endod 2005; 100: 40-51; Miller C S, White D K, Royse D D. In situ hybridization analysis of human papillomavirus in orofacial lesions using a consensus biotinylated probe. Am J Dermatopathol 1993; 15:256-9; Yildirim B, Senguven B, Demir C. Prevalence of herpes simplex, Epstein Barr and human papilloma viruses in oral lichen planus. Medicina oral, patologia oral y cirugia bucal 2011; 16:e170-4).

So far, the lack of any study using accurate tools to address the specificity of lesional CTLs in OLP precludes any conclusion about mechanisms underlying this dysregulation of muco-cutaneous T-cell immune responses. Thus, there is need in the art for compositions and methods for diagnosis and treatment of severe erosive OLP.

BRIEF SUMMARY OF THE INVENTION

The invention encompasses compositions and methods for the diagnosis and treatment of OLP patients.

The invention encompasses a method for monitoring treatment of an OLP patient. In one embodiment, the method comprises providing a cell sample, preferably a lesion or a blood sample, from an OLP patient, detecting the presence of a human papilloma virus (HPV) or an immune response against a human papilloma virus infection in the cell sample, treating the patient with an anti-HPV treatment or anti-HPV drug, preferably cidofovir, and, optionally, detecting a reduction in an OLP symptom. In some embodiments the human papilloma virus is of a type selected from types 16, 18, 31, 33, 35, 39, 45, 51, 52, 56, 58, 59, 68, 69, 73, and 82. In some embodiments the anti-HPV treatment or anti-HPV drug is selected from a composition comprising the major capsid protein L1 of HPV types 6, 11, 16, and 18; a composition comprising the major capsid protein L1 of HPV types 16, and 18; and at least one chimeric recombinant Bordetella sp. adenylate cyclase (CyaA) protein or fragment thereof, the CyaA protein or fragment thereof comprising at least one inserted human papilloma virus (HPV) E7 epitope.

In one embodiment, the presence of an immune response against a human papilloma virus infection is detected by contacting the sample with at least one HPV peptide, more particularly at least one E7 HPV peptide, preferably at least one peptide comprising the amino acid sequence YMLD-LQPETT (SEQ ID NO:29).

In one embodiment, the presence of an immune response against a human papilloma virus infection is detected by sequencing the CDR3β sequence of the TCRVβ3 gene segment in the T cells of the cell sample. Preferably, the CDR3β sequence of the TCRVβ3 gene segment in the T cells of the cell sample comprises any one of SEQ ID NOs 1-10.

In one embodiment, the presence of an immune response against a human papilloma virus infection is detected by detecting a clonal population of CD8+ TCRVβ3+ T cells in the cell sample.

In one embodiment, the presence of a human papilloma virus is detected by preparing nucleic acids from the cell sample and contacting the nucleic acids with at least one HPV specific primer or probe.

The invention encompasses methods for in vitro diagnosing an OLP patient from a cell sample thereof. In one embodiment, the method comprises providing a cell sample, preferably a lesion or a blood sample, from an OLP patient, contacting the sample with at least one HPV peptide; and detecting the interaction between the HPV peptide and cells in the sample. Preferably, the HPV peptide comprises the amino acid sequence YMLDLQPETT (SEQ ID NO:29). The step of providing a cell sample is optional in the in vitro diagnostic methods according to the present invention.

The method can comprise preparing nucleic acids from the cell sample and contacting the nucleic acids with an HPV specific primer or probe.

The methods of the invention can comprise treating the patient with an anti-HPV treatment or anti-HPV drug, providing a second cell sample from an OLP patient, contacting the sample with at least one HPV peptide; and detecting the interaction between the HPV peptide and cells in the sample.

In one embodiment, the method comprises providing a blood sample from an OLP patient, isolating T cells from the blood sample, and detecting CDR3β distribution of the TCRVβ3 gene segment in the T cells.

The method can comprise treating the patient with an anti-HPV treatment or anti-HPV drug, preferably cidofovir, and providing a second blood sample from an OLP patient, isolating T cells from the blood sample, and detecting CDR3β distribution of the TCRVβ3 gene segment in the T cells. The method can comprise preparing nucleic acids from the blood sample and contacting the nucleic acids with an HPV specific primer or probe.

In one embodiment, the method comprises providing a blood sample from an OLP patient, isolating T cells from the blood sample, and determining the CDR3β sequence of the TCRVβ3 gene segment in the T cells. Preferably, the CDR3β sequence of the TCRVβ3 gene segment in the T cells of the cell sample comprises any one of SEQ ID NOs 1-10.

In one embodiment, the method comprises treating the patient with an anti-HPV treatment or anti-HPV drug preferably cidofovir, and providing a second blood sample from an OLP patient; isolating T cells from the blood sample; and determining the CDR3β sequence of the TCRVβ3 gene segment in the T cells.

The method can comprise preparing nucleic acids from the cell sample and contacting the nucleic acids with an HPV specific primer or probe.

The invention encompasses methods for treating an OLP patient. In one embodiment, the method comprises providing a blood sample from an OLP patient, isolating T cells from the blood sample, detecting a clonal population of CD8+ TCRVβ3+ T cells, and treating the patient with a compound specific for the CD8+ TCRVβ3+ T cells.

The invention encompasses a method comprising treating the patient with (i) an anti-HPV treatment or anti-HPV drug, preferably cidofovir, and (ii) a steroid treatment, immunosuppressant treatment, or photochemotherapy.

The invention encompasses the use of a compound specific for CD8+ TCRVβ3+ T cells for the treatment of OLP.

The invention also encompasses a method for treating an oral lichen planus patient comprising selecting an HPV positive oral lichen planus patient; and treating the HPV positive oral lichen planus patient with extracorporeal photochemotherapy (ECP). In some embodiments the human papilloma virus is a high risk HPV virus. In some embodiments the human papilloma virus is of a type selected from types 16, 18, 31, 33, 35, 39, 45, 51, 52, 56, 58, 59, 68, 69, 73, and 82.

The invention also encompasses a method for treating an oral lichen planus patient comprising selecting an HPV positive oral lichen planus patient; and treating the HPV positive oral lichen planus patient with a treatment selected from a composition comprising the major capsid protein L1 of HPV types 6, 11, 16, and 18; a composition comprising the major capsid protein L1 of HPV types 16, and 18; and at least one chimeric recombinant Bordetella sp. adenylate cyclase (CyaA) protein or fragment thereof, the CyaA protein or fragment thereof comprising at least one inserted human papilloma virus (HPV) E7 epitope. In some embodiments the human papilloma virus is a high risk HPV virus. In some embodiments the human papilloma virus is of a type selected from types 16, 18, 31, 33, 35, 39, 45, 51, 52, 56, 58, 59, 68, 69, 73, and 82.

The invention further concerns an anti-HPV drug for use in any one of the aforementioned methods.

BRIEF DESCRIPTION OF THE DRAWINGS

FIG. 6 depicts characteristics of the studied patients.

FIG. 8 summarizes the data obtained in 4 OLP patients.

DETAILED DESCRIPTION OF THE INVENTION

Figure 1:
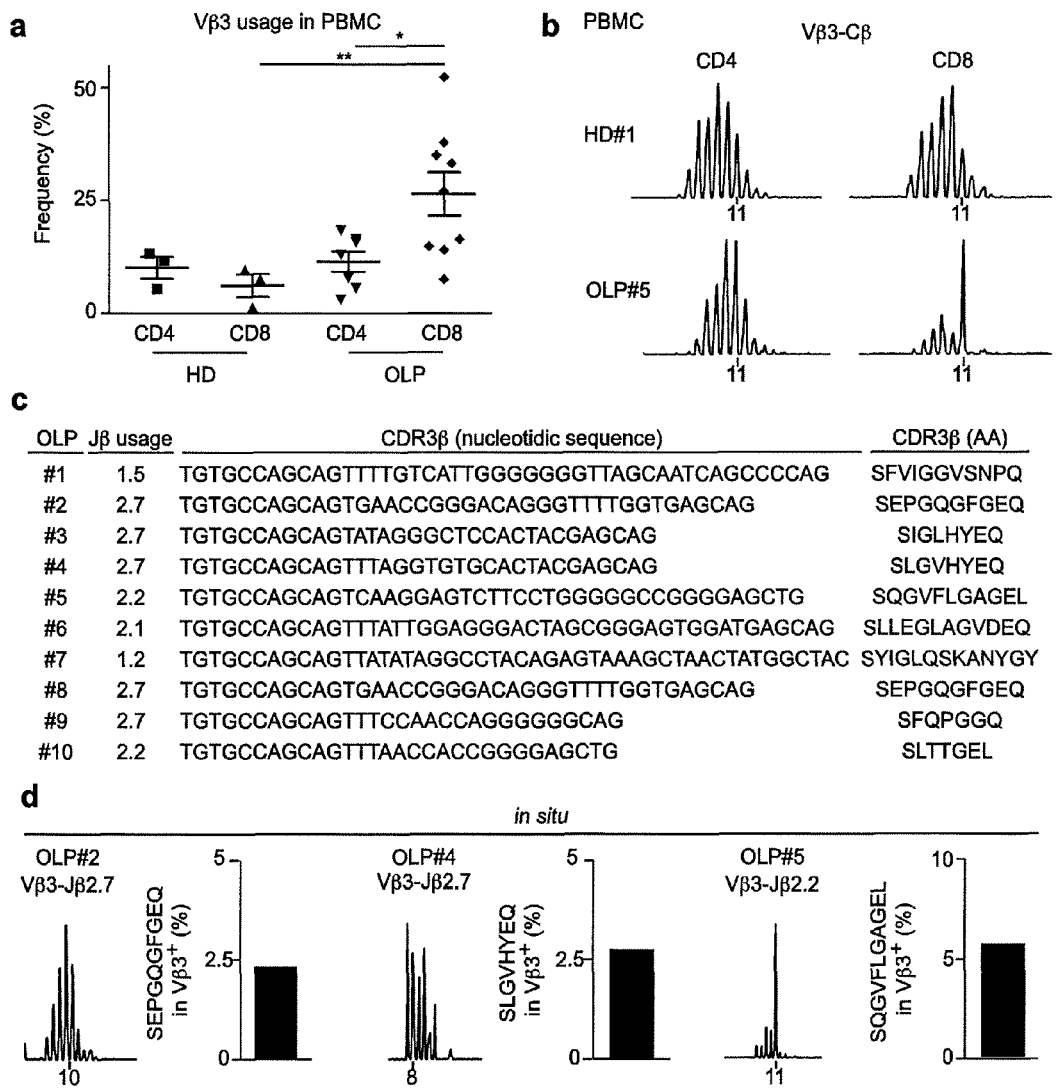
FIGS. 1a-d depict TCRVβ3+ clonal expansions skewed CD8+ T-cell repertoires of OLP patients. RT-PCR amplifications analysis of the TCRVβ3 usage in CD4+ and CD8+ T cells from the blood of HD or OLP patients (a). CDR3β length distributions for CD4+ and CD8+ Vβ3-Cβ rearrangements from HD1 and OLP#5. The peak of the $11^{th}$ codon is marked on the abscissa axis (b). Table of clonotypes for each OLP patient (SEQ ID NOs:1-20) (c). CDR3β length distributions for Vβ3-Jβ2.7 rearrangements from OLP#2 and #4 lichen lesions and Vβ3-Jβ2.2 from OLP#5 lichen lesion as well as clonotype distribution estimated by CDR3 sequencing (d). * $p<0.05$, ** $p<0.01$

To investigate the molecular mechanisms underlying dysregulation of T-cell immune responses in patients with OLP, the diversity and antigen-specificity of the T-cell receptor (TCR) expressed by CD8+ T-cells was studied using spectratyping, TCR sequencing and cell sorting using dextramers in 10 OLP patients undergoing extracorporeal photochemotherapy (ECP).

Expansions of TCRVβ3 bearing activated CD8+ T-cells were found in peripheral blood and in lesional tissues of OLP patients. Spectratyping and sequencing studies identified distinct and common clonotypes in each patient. This expansion was enriched with Human Papilloma Virus (HPV) 16-specific CD8+ T-cells as shown by their immunerecognition of the $E7_{11-20}$ immunodominant epitope in HLA-A2 patients. Under treatment with ECP, clonotypic CD8+ T-cell expansions decreased while clinical remission was reached in the vast majority of patients.

Consequently, a massive clonal expansion of activated CD8+ T-cells with increased frequency of HPV 16-specific CD8+ T-cells is a characteristic of OLP. This indicates a causal link between HPV infection and the dysimmune process. Massive clonal expansions of CD8+ T-cells in both peripheral blood and mucous membranes and/or skin lesions of patients with erosive OLP were found. The pathogenic relevance of these TCRVβ3+ clonotypic expansions is demonstrated by their consistent presence in all studied patients, their activated phenotype, and by their decrease in peripheral blood from several patients entering PR or CR under ECP, becoming even undetectable in 3 patients.

The cytotoxic profile of the clonotypic peripheral CD8 T-cell expansions, which include HPV-specific cells was also characterized. It is revealed herein that, following ECP, a specific priming for massive apoptosis is detected in the $CD3^+CD8^+Vβ3^+$ T-cell subset, whereas this priming was not detected in the general CD8 and CD4 T cell populations. These results demonstrate the involvement of HPV-specific $CD8^+Vβ3^+$ T cells in the killing of autologous cells in OLP lesions, and they suggest for the first time that ECP-induced remission is associated with the priming for apoptosis of these killer cells.

The relevance of this set of data is strengthened by two previous studies, one reporting the increased presence of TCRVβ3 and TCRVα2 positive cells in the oral mucosal T-cell infiltrate of 7 OLP patients (Simark-Mattsson C, Bergenholtz G, Jontell M, Tarkowski A, Dahlgren U I. T cell receptor V-gene usage in oral lichen planus; increased frequency of T cell receptors expressing V alpha 2 and V beta 3. Clin Exp Immunol 1994; 98:503-7), and the more recent study of 12 OLP patients showing that CD8+ T-cells had skewed TCR repertoire towards the usage of a restricted set of TCRVβ segments including TCRVβ3 (Gotoh A, Hamada Y, Shiobara N, et al. Skew in T cell receptor usage with polyclonal expansion in lesions of oral lichen planus without hepatitis C virus infection. Clin Exp Immunol 2008; 154:192-201). However, no clonal expansions were found in these patients and these latter studies did not address the antigen specificity of activated CD8+ T-cells in OLP. The present study's detection in peripheral blood and in lesion from HLA-A2+ OLP patients of an increased population of activated CD8+ T-cells recognizing the HPV16 $E7_{11-20}$ epitope has important consequences for the understanding of OLP pathogenesis, notably the contribution of HPV.

It was previously shown that CTL clones from OLP lesions showed dose-dependent killing of HPV type 16 immunodominant peptides (E6 and E7)-immortalized autologous lesional and normal keratinocytes, but no cytotoxic activity against Epstein-Barr virus-transformed autologous B-cell blast (Sugerman P B, Satterwhite K, Bigby M. Autocytotoxic T-cell clones in lichen planus. The British journal of dermatology 2000; 142:449-56). One key observation establishing a link between HPV and selected TCRVβ3 CD8+ T-cells in the presently studied patients is the enrichment of detected clonotypes in CD8+ T-cells stained with HLA-A2-HPV dextramer. Indeed, these results are reminiscent of results from previous in vitro studies showing the capacity of this $E7_{11-20}$ HPV16 epitope to favor the stimulation and expansion of CTL clones expressing TCRVβ3, without evidence of HLA class I restriction (Schreurs M W, Scholten K B, Kueter E W, Ruizendaal J J, Meijer C J, Hooijberg E. In vitro generation and life span extension of human papillomavirus type 16-specific, healthy donor-derived CTL clones. J Immunol 2003; 171:2912-21; Nilges K, Hohn H, Pilch H, et al. Human papillomavirus type 16 E7 peptide-directed CD8+ T cells from patients with cervical cancer are cross-reactive with the coronavirus NS2 protein. J Virol 2003; 77:5464-74). This set of data also raises the HPV infection status in OLP patients.

Likewise, a large set of published HPV detection studies support a pathogenic contribution of some HPV subtypes in OLP. Notably, detection of viral DNA mainly derived from HPV6/11/16/31/33 has been reported in mucosal oral and/or genital lesions from OLP patients in several studies including the present one, providing a rationale for their role as putative antigenic stimuli (Lodi G, Scully C, Carrozzo M, Griffiths M, Sugerman P B, Thongprasom K. Current controversies in oral lichen planus: report of an international consensus meeting. Part 1. Viral infections and etiopathogenesis. Oral Surg Oral Med Oral Pathol Oral Radiol Endod 2005; 100:40-51; Mattila R, Rautava J, Syrjanen S. Human papillomavirus in oral atrophic lichen planus lesions. Oral oncology 2012; 48:980-4). This latter hypothesis has been reinforced by a recent exhaustive systematic review of HPV detection in 39 selected cross-sectional studies, showing that HPV DNA is significantly more frequently detected in OLP lesions compared to controls with mean odds ratio exceeding 5 (Syrjanen S, Lodi G, von Bultzingslowen I, et al. Human papillomaviruses in oral carcinoma and oral potentially malignant disorders: a systematic review. Oral diseases 2011; 17 Suppl 1:58-72).

Indeed, the positive detection of prior or current infection with HPV16 in 2/6 of the patients, including 1 patient who showed clear expansion of HPV16 $E7_{11-20}$ specific cells in blood and lesional mucosa, is a strong support for the contribution of HPV as an antigenic stimulus of CD8+ T-cell expansion that characterizes severe erosive OLP. Finally, the presence of HPV16 $E7_{11-20}$ specific CD8+ T-cells in the vicinity of dying epithelial cells in a studied patient correlates with their potential involvement in tissue damage of OLP, even though this latter observation does not rule out the deleterious role of other subtypes than HPV16 that were not addressed in the patients by dextramer and/or serological immunological studies. As some of the patients did not show either presence of HPV16 DNA or serological evidence of prior HPV16 infection, other HPV subtypes or even alternative viral agents such as Epstein Barr virus might be able to trigger similar CTL expansions in OLP (Lodi G, Scully C, Carrozzo M, Griffiths M, Sugerman P B, Thongprasom K. Current controversies in oral lichen planus: report of an international consensus meeting. Part 1. Viral infections and etiopathogenesis. Oral Surg Oral Med Oral Pathol Oral Radiol Endod 2005; 100:40-51).

As most adult individuals are infected at some point with one or several HPV subtypes, the present results also raise the mechanisms underlying dysimmunity in OLP patients. Supporting the autoimmune hypothesis and its possible link with HPV is the previously established presence among lesional T-lymphocytes of 2 OLP patients of CTL clones reacting towards autologuous keratinocytes immortalized with HPV 16 E6 and E77. It is worth to notice that a causal role for HPV infection in OLP does not necessarily require constant tissue viral replication over time, as an initial viral stimulation might be sufficient to trigger the founder immune response, with following autoimmune T-cell expansions related to molecular mimicry, unsequestration of masked self epitopes or both (Selmi C, Leung P S, Sherr D H, et al. Mechanisms of environmental influence on human autoimmunity: a National Institute of Environmental Health Sciences expert panel workshop. J Autoimmun 2012; 39:272-84). As such, it can explain why antibodies to HPV16 were detected in the sera of only 2 patients of the cohort. In line with the former of these hypotheses, molecular mimicry between HPV16 E7 protein and human self has been revealed by computer based analyses, providing a rational basis for further investigations of OLP lesional CTL regarding their immunoreactivity towards HPV versus self candidate antigens (Natale C, Giannini T, Lucchese A, Kanduc D. Computer-assisted analysis of molecular mimicry between human papillomavirus 16 E7 oncoprotein and human protein sequences. Immunol Cell Biol 2000; 78:580-5). However, alternative mechanisms such as alterations of the TCRVβ3+/HLA-peptide synapse by some viral products cannot be ruled out. Finally, it also remains to be determined if HPV and/or other viral stimuli are involved in other forms of lichen planus. In the meantime, the present data pave the way for innovative diagnostic, prophylactic, and therapeutic strategies in OLP.

The invention encompasses compositions and methods for the diagnosis and treatment of OLP patients and the use of compounds to treat OLP. The diagnosis can be made by detecting the presence of a human papilloma virus and/or by detecting an immune response against an HPV infection. The invention further encompasses methods for detecting a reduction in an OLP symptom and methods for monitoring treatment of an OLP patient.

The invention encompasses compositions and methods for the diagnosis of an HPV infection in an OLP patient comprising detecting a T cell response against an HPV infection. The methods can further comprise detecting the presence of a human papilloma virus nucleic acid using a probe or primer.

Methods for Diagnosing an Oral Lichen Planus Patient

The invention encompasses methods for the in vitro diagnosis of OLP patients. Based on the discovery that a massive clonal expansion of activated CD8+ T-cells with increased frequency of HPV 16-specific CD8+ T-cells is a characteristic of OLP, OLP patients can be diagnosed based on a cell sample from an oral lichen planus patient. In a preferred embodiment, the method comprises detecting the presence of a human papilloma virus or an immune response against a human papilloma virus infection in a cell sample from an oral lichen planus patient. The method can optionally comprise a preliminary step of providing such a cell sample.

Preferably, the clonal expansion of activated CD8+ T-cells, preferably of CD8+ TCRVβ3+ T cells, is measured by routine techniques in the art. For example, the techniques described in the examples can be used.

Cell Sample

The cell sample can be any cell sample obtained from an OLP patient. Preferably, the cell sample is generated by drawing blood, with a cytobrush, or by taking a biopsy. The cell sample is preferably a blood sample, most preferably isolated peripheral blood mononuclear cells (PBMCs), or isolated T cells. The sample can be a lymph or synovial fluid. The PBMC and T cells can be isolated by routine techniques in the art. For example, the techniques described in the examples can be used.

The cell sample can be a tissue sample, preferably, a lesion from an OLP patient. The tissue sample can be a paraffin section or thin section of a lesion.

Immune Response Against HPV Infection

The invention encompasses detecting an immune response against an HPV infection. In one embodiment, the method comprises providing a cell sample from an OLP patient, contacting the sample with an HPV peptide, and detecting the interaction between the HPV peptide and cells in the sample. Contacting the HPV peptide with a cell sample and detecting its interaction can be performed by routine techniques in the art. For example, the techniques described in the examples and below can be used.

The method can further comprising treating the patient with an anti-HPV treatment or anti-HPV drug, preferably, cidofovir, and subsequently providing a second cell sample from the OLP patient and repeating the step of detecting an immune response against an HPV infection.

Preferably, the HPV peptide comprises at least one HPV E6 or E7 peptide recognized by T cells, particularly CD8+ T cells. In a preferred embodiment, the HPV peptide comprises one or several peptides comprising any one of the following amino acid sequences: HYNIVTFCC (SEQ ID NO:21), KLCLRFLSK (SEQ ID NO:22), KPTLKEYVL (SEQ ID NO:23), LLMGTLGIVC (SEQ ID NO:24), MLDLQPETT (SEQ ID NO:25), NTLEQTVKK (SEQ ID NO:26), RAHYNIVTF (SEQ ID NO:27), VPTLQDVVL (SEQ ID NO:28), and YMLDLQPETT (SEQ ID NO:29).

The method can comprise treating an OLP patient with a steroid treatment, immunosuppressant treatment, or photochemotherapy, providing a cell sample from the OLP patient and detecting an immune response against an HPV infection.

MHC Multimer Staining Assay

The method can comprises an MHC multimer staining assay, for example as in Zentz et al., Human Immunology 68, 75-85 (2007) and Hoffmann et al., Int. J. Cancer: 118, 1984-1991 (2006). Since HPV-tetramer+ T cells remain many months or even years after viral clearance, multimer staining may represent a more sensitive method of HPV infection than detection of the virus itself. Wang et al., Clinical and Vaccine Immunology, Vol. 15, No. 6, June 2008, p. 937-945. Each of these references are incorporated by reference with respect to the multimer staining assays disclosed therein. MHC multimer staining assays can be performed by routine techniques in the art. For example, the techniques described in the examples and in the cited references.

T cells carry T-cell receptors (TCRs) that recognize specific MHC-peptide complexes displayed on the surface of antigen presenting cells. This specific interaction between T cells and MHC-peptide complexes has been used to detect and isolate distinct populations of T cells with specificity for a given MHC-peptide complex. MHC multimers are reagents that carry multiple MHC-peptide complexes, and thus have the ability to bind simultaneously to multiple TCRs on a single T cell, allowing for a stable interaction between the reagent and the T cell. MHC multimers can be used to detect and quantify antigen-specific T cells in fluid samples (e.g. blood, cultured cell lines, CSF, lymph, synovial fluid) by flow cytometry, and can be used for in situ detection (e.g. in solid tumors) using immunohistochemistry (IHC). MHC multimers may also be used to isolate antigen-specific T-cell populations.

MHC Dextramer® reagents (Immudex), or other similar MHC multimers, can be used. These are fluorescent labeled MHC multimers that can be used to detect antigen-specific T cells in fluid cell samples and solid tissue samples. The MHC Dextramer™ reagents come with any of three different fluorochromes (PE, APC or FITC). When using flow cytometry they may be used to accurately monitor CD8+ T-cell responses in blood, CSF or other fluid cell samples.

In one embodiment, a labeled HPV peptide is contacted with a thin section of a tissue sample, preferably, a lesion from an OLP patient. The HPV peptide can bind to a specific TCR on the T cells in the sample. After contacting the HPV peptide with the cell sample, the unbound is removed and the HPV peptide bound to the cells in the cell sample is detected. The method can be performed by routine techniques in the art. For example, the techniques described in the examples can be used. In one embodiment, cryopreserved sections are dried, fixed in acetone, incubated with TRITC-labeled anti-CD8 antibody followed by incubation with FITC-labeled Dextramer, and nuclei counter-stained with DAPI. A preferred HPV peptide is YMLDLQPETT (SEQ ID NO:29).

Whole Blood Staining Procedure for MHC Multimers

Human peripheral whole blood can be stained with MHC Multimers, particularly MHC Dextramers™ simultaneously with immuno-phenotyping of relevant antigens, using the following protocol: Transfer 100 µL whole blood to a 12×75 mm polystyrene test tube. Add 10 µl of MHC Dextramer™ and mix with a vortex mixer. Incubate in the dark at room temperature for 10 minutes. Add an optimally titrated amount of anti-CD8 antibody (e.g. Dako clone DK25) conjugated with relevant fluorochromes and mix well. Continue incubation at 2-8° C. in the dark for 20 minutes. The staining procedure describes the use of CD8 antibody together with MHC Dextramers™. Additional antibodies for detection of extracellular antigens can be added. Add 2 mL EasyLyse™ working solution (Dako code S2364) and incubate for 10 minutes. Add 2 mL 0.01 mol/L PBS and centrifuge for 5 minutes at 300×g and aspirate supernatant.

Re-suspend pellet in an appropriate fluid for flow cytometry, e.g. 0.4 mL PBS, and analyze on a flow cytometer or store at 2-8° C. in the dark until analysis. Do not store longer than 2 hours before analysis. A preferred HPV peptide is YMLDLQPETT (SEQ ID NO:29). The assay can also be used with other cell types mentioned herein.

TCR Assays

In one embodiment, the method comprises providing a blood sample from an oral lichen planus patient, isolating T cells from the blood sample, and detecting CDR3β distribution of the TCRVβ3 gene segment in the T cells. In a preferred embodiment, the oligoclonal spectratyping pattern (See, e.g., Nilges et al., Journal of Virology, May 2003, p. 5464-5474 Vol. 77, No. 9, incorporated by reference) of Vβ3 TCR repertoire of sorted CD8 T cells is detected using cDNA after amplification with Vβ3 and Cβ specific primers.

In one embodiment, RNA from cells is extracted and reverse-transcribed into cDNA. Quantitative PCR amplifications are then done and spectratyping analysis of each Vβ-Cβ rearrangement performed. Usage of Vβ gene segment, and more particularly Vβ3, can be used to determine whether clonal expansion exists in the tested patient. CDR3β length distribution profile allows characterization of a polyclonal T cell population (i.e., a bell-shaped curve) or an oligloconal or monoclonal T cell population (i.e., a disturbed Gaussian-like curve with one or few peaks).

Thus, the method can comprise isolating RNA from cells of an OLP patient, reverse-transcribing the RNA into cDNA, amplifying the DNA, and determining whether clonal expansion of a T cell population exists. Preferably, a Vβ gene segment, more particularly Vβ3, is amplified.

The method can further comprise treating the patient with an anti-HPV treatment or anti-HPV drug, preferably, cidofovir, and subsequently providing a second cell sample from the OLP patient, isolating T cells from the blood sample, and detecting CDR3β distribution of the TCRVβ3 gene segment in the T cells.

The method can comprise specific expansion in the blood of TCR Vß3+CD8+ T cells, detection by quantitative PCR using the 24 Vß-specific primers on sorted CD8+ T cells, or by flow cytometry on total blood with CD8- and Vß3-specific antibodies.

In various embodiments, the methods used in Lim et al., J Immunol Methods. 2002 Mar. 1; 261(1-2):177-94; Blattman et al., The Journal of Immunology Dec. 1, 2000 vol. 165 no. 11 6081-6090; and Alvarez et al., Am J Transplant. 2005 April; 5 (4 Pt 1):746-56, which are incorporated by reference herein, can be used.

In one embodiment, the method comprises providing a blood sample from an OLP patient; optionally isolating T cells from the blood sample, and determining the CDR3β sequence of the TCRVβ3 gene segment in the T cells.

Any sequencing method known in the art can be employed. As used herein, the term "sequencing" is used in a broad sense and refers to any technique known by the skilled person including but not limited to Sanger dideoxy termination sequencing, whole-genome sequencing, sequencing by hybridization, pyrosequencing, capillary electrophoresis, cycle sequencing, single-base extension sequencing, solid-phase sequencing, high-throughput sequencing, massively parallel signature sequencing (MPSS), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof. In specific embodiments, the method of the invention is adapted to run on ABI PRISM® 377 DNA Sequencer, an ABI PRISM® 310, 3100, 3100-Avant, 3730, or 3730×1 Genetic Analyzer, an ABI PRISM® 3700 DNA Analyzer, or an Applied Biosystems SOLiD™ System (all from Applied Biosystems), a Genome Sequencer 20 System (Roche Applied Science).

Preferably, the CDR3β sequence of the TCRVβ3 gene segment in the T cells of the cell sample encodes any one of the amino acid sequences of SEQ ID NOs 1-10 or comprises any one of the nucleic acid sequences of SEQ ID NOs 11-20:

```
SFVIGGVSNPQ,                                    (SEQ ID NO: 1)

SEPGQGFGEQ,                                     (SEQ ID NO: 2)

SIGLHYEQ,                                       (SEQ ID NO: 3)

SLGVHYEQ,                                       (SEQ ID NO: 4)

SQGVFLGAGEL,                                    (SEQ ID NO: 5)

SLLEGLAGVDEQ,                                   (SEQ ID NO: 6)

SYIGLQSKANYGY,                                  (SEQ ID NO: 7)

SEPGQGFGEQ,                                     (SEQ ID NO: 8)

SFQPGGQ,                                        (SEQ ID NO: 9)

SLTTGEL,                                        (SEQ ID NO: 10)

TGTGCCAGCAGTTTTGTCATTGGGGGGGTTAGCAATCAGCCCCAG,  (SEQ ID NO: 11)

TGTGCCAGCAGTGAACCGGGACAGGGTTTTGGTGAGCAG,        (SEQ ID NO: 12)

TGTGCCAGCAGTATAGGGCTCCACTACGAGCAG,              (SEQ ID NO: 13)

TGTGCCAGCAGTTTAGGTGTGCACTACGAGCAG,              (SEQ ID NO: 14)

TGTGCCAGCAGTCAAGGAGTCTTCCTGGGGGCCGGGGAGCTG,     (SEQ ID NO: 15)

TGTGCCAGCAGTTTATTGGAGGGACTAGCGGGAGTGGATGAGCAG,  (SEQ ID NO: 16)

TGTGCCAGCAGTTATATAGGCCTACAGAGTAAAGCTAACTATGGCTAC, (SEQ ID NO: 17)

TGTGCCAGCAGTGAACCGGGACAGGGTTTTGGTGAGCAG,        (SEQ ID NO: 18)

TGTGCCAGCAGTTTCCAACCAGGGGGGCAG,                 (SEQ ID NO: 19)
and

TGTGCCAGCAGTTTAACCACCGGGGAGCTG.                 (SEQ ID NO: 20)
```

In one embodiment, the method comprises detecting any of the nucleic acid sequences of SEQ ID NO:s 11-20 or any nucleic acid sequence encoding any of the amino acid sequences of SEQ ID NOs 1-10. These sequences can be specifically detected by numerous techniques known in the art, such as sequencing, hybridization, or amplification assays.

For example, the amplification method can be RCA, MDA, NASBA, TMA, SDA, LCR, b-DNA, PCR (all forms including RT-PCR), RAM, LAMP, ICAN, SPIA, QB-replicase, or Invader. A preferred amplification method is the polymerase chain reaction (PCR) amplification. See, e.g., PCR Technology: Principles and Applications for DNA Amplification (Ed. H. A. Erlich, Freeman Press, NY, N.Y., 1992); PCR Protocols: A Guide to Methods and Applications (Eds. Iinis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675.

Other preferred amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), and nucleic acid based sequence amplification (NABSA) (U.S. Pat. Nos. 5,130,238, 5,409,818, 5,554,517, and 6,063,603). Other amplification methods that may be used are described in U.S. Pat. Nos. 5,242,794, 5,494,810, 4,988,617 and 6,582,938. The above references regarding amplification of nucleic acids are specifically incorporated by reference with respect to the disclosure therein of the specific reaction conditions used for amplification in each of the amplification methods.

The method can further comprise treating the patient with an anti-HPV treatment or anti-HPV drug, preferably, cidofovir, and subsequently providing a second blood sample from an OLP patient, and determining the CDR3β sequence of the TCRVβ3 gene segment in the T cells in the blood sample.

The methods can be performed by routine techniques in the art. For example, the techniques described in the examples can be used.

HPV Detection

The invention encompasses methods of detecting the presence or absence of a human papilloma virus. The method can comprise detecting the presence or absence of HPV DNA, RNA, or protein in an OLP patient sample. The method can comprise preparing nucleic acids from the cell sample and contacting the nucleic acids with an HPV specific primer or probe. The nucleic acids can be DNA and/or RNA. The method can be performed by routine techniques in the art. For example, the techniques described in the examples can be used.

The invention encompasses the use of techniques for detecting HPV based on DNA typing. For example, the COBAS (Roche) and APTIMA (GEN-PROBE) kits are PCR tests of specific targets intended for the qualitative in vitro detection of mRNA of the L1 gene from 17 types of human papillomavirus (HPV) virus considered High risk (HPV 16, 18, 31, 33, 35, 39, 45, 51, 52, 56, 58, 59, 66, 68, 69, 73, and 82). 6 different results are obtainable: HPV16 positive or negative, HPV18 positive or negative, others 12 HPVs positive or negative. LINEAR ARRAY HPV Genotyping Test (Roche) is a qualitative test that detects 37 high- and low-risk human papillomavirus genotypes, including those considered a significant risk factor for High-grade Squamous Intraepithelial (HSIL) progression to cervical cancer. This test is a qualitative in vitro test for the detection of Human Papilloma Virus in clinical specimens. The test utilizes amplification of target DNAs by PCR of the late gene L1 of HPV DNA genotypes 6, 11, 16, 18, 26, 31, 33, 35, 39, 40, 42, 45, 51, 52, 53, 54, 55, 56, 58, 59, 61, 62, 64, 66, 67, 68, 69, 70, 71, 72, 73 (MM9) (novel type related to HPV73), 81, 82 (MM4) (novel type related to HPV82), 83 (MM7) (novel type related to HPV83), 84 (MM8) (novel type related to HPV84), IS39 and CP6108. The digene HC2 HPV DNA Test, developed by Qiagen, is based on Capture Hybridization of HPV DNAs (L1 gene) for the qualitative detection of 18 types (HPV 16, 18, 26, 31, 33, 35, 39, 45, 51, 52, 53, 56, 58, 59, 66, 68 [68a], 73, 82MM4 [82IS39]) in cervical specimens.

More recently, NucliSENS EasyQ HPV was made available to qualitative detection of oncogenes E6/E7 mRNAs of 5 specific High risk HPVs 16, 18, 31, 33 and 45. Detection of HPV E6 and E7 has been proposed as a better correlate of cancer development than HPV DNA.

In addition, WO2011/088573, describes a set of probes to detect and Identify 46 specifically targeted species of mucosal human papillomaviruses (HPV). These probes are used as a multiplex assay based on nested PCR amplification and the Luminex xMAP technology for genotyping DNA of L1 genes of HPV types 6, 11, 13, 16, 18, 26, 30, 31, 32, 33, 35, 39, 40, 42, 43, 44, 45, 51, 52, 53, 54, 56, 58, 59, 61, 62, 66, 67, 68, 69, 70, 71, 72, 73, 74, 81, 82, 83, 84, 85, 86, 87, 89, 90, 91 and 97.

HPV can also be detected by preparing a nucleic acid from cells from an OLP patient and sequencing the HPV nucleic acid. Any sequencing method known in the art can be employed.

HPV can also be detected by methods comprising sequencing HPV nucleic acids present in a sample of a subject. In some embodiments all or part of the E6 and/or E7 region of an HPV nucleic acid is sequenced. As used herein, the term "sequencing" is used in a broad sense and refers to any technique known by the skilled person including but not limited to Sanger dideoxy termination sequencing, whole-genome sequencing, sequencing by hybridization, pyrosequencing, capillary electrophoresis, cycle sequencing, single-base extension sequencing, solid-phase sequencing, high-throughput sequencing, massively parallel signature sequencing (MPSS), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof. In specific embodiments, the method and kit of the invention is adapted to run on ABI PRISM® 377 DNA Sequencer, an ABI PRISM® 310, 3100, 3100-Avant, 3730, or 3730×1 Genetic Analyzer, an ABI PRISM® 3700 DNA Analyzer, or an Applied Biosystems SOLiD™ System (all from Applied Biosystems), a Genome Sequencer 20 System (Roche Applied Science), an HiSeq 2500, an HiSeq 2000, a Genome Analyzer IIx, a MiSeq Personal Sequencer, a HiScanSQ (all from Illumina), the Genetic Analysis System, including the Single Molecule Sequencer, Analysis Engine and Sample Loader (all from HeliScope), the Ion Proton™ Sequencer, or the Ion PGM™ Sequencer (both from Ion Torrent).

For all technologies described herein, although in some embodiments the primers are used in solution, in other embodiments the primers are linked to a solid support.

To permit its covalent coupling to the support, the primer is generally functionalized. Thus, it may be modified by a thiol, amine or carboxyl terminal group at the 5' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine links between the primer and the support. Any other method known to a person skilled in the art may be used, such as bifunctional coupling reagents, for example.

Moreover, to improve the hybridization with the coupled oligonucleotide, it can be advantageous for the oligonucleotide to contain an "arm" and a "spacer" sequence of bases. The use of an arm makes it possible, in effect, to bind the primer at a chosen distance from the support, enabling its conditions of interaction with the DNA to be improved. The arm advantageously consists of a linear carbon chain, comprising 1 to 18 and preferably 6 or 12 (CH2) groups, and an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence GAGG. The arm is advantageously composed of a linear carbon chain comprising 6 or 12 carbon atoms.

For implementation of the present invention, different types of support may be used. These can be functionalized chromatographic supports, in bulk or prepacked in a column, functionalized plastic surfaces or functionalized latex beads, magnetic or otherwise. Chromatographic supports are preferably used. As an example, the chromatographic supports capable of being used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

In some embodiments, the invention is aimed at a method for determining a profile of sequences in one or more samples of patients suspected to be infected with or carrying an HPV, comprising detecting HPV sequences in one or more samples comprising: a) amplifying nucleic acid molecules in the sample; b) spatially isolating individual molecules of said amplified nucleic acid molecules; c) optionally re-amplifying said amplified nucleic acid molecules; d) sequencing said re-amplified nucleic acid molecules; and e) determining the levels of different sequences from said sample to generate said profile of nucleic acid molecules in the sample. Said amplifying and/or re-amplifying comprises PCR, multiplex PCR, TMA, NASBA, or LAMP and spatially isolating individual molecules comprises separating molecules in two dimensions on a solid support, separating said molecules in three dimensions for example in a solution with micelles, or separating molecules using micro-reaction chambers. Said sequencing in step d) comprises dideoxy sequencing, sequencing by synthesis using reversibly terminated labeled nucleotides, pyrophosphate release on nucleotide incorporation, sequencing by synthesis using allele specific hybridization to a library of labeled oligonucleotide probes followed by ligation of said probes, real time monitoring of the incorporation of labeled nucleotides during a polymerization step.

Such amplification techniques include in particular isothermal methods and PCR-based techniques. Isothermal techniques include such methods as e.g. nucleic acid sequence-based amplification (NASBA), loop-mediated isothermal amplification (LAMP), helicase-dependent amplification (HDA), rolling circle amplification (RCA), and strand displacement amplification (SDA), exponential amplification reaction (EXPAR), isothermal and chimeric primer-initiated amplification of nucleic acids (ICANs), signal-mediated amplification of RNA technology (SMART) and others (see e.g. Asiello and Baeumner, Lab Chip; 11(8): 1420-1430, 2011). Preferably, the PCR technique used quantitatively measures starting amounts of DNA, cDNA, or RNA. Examples of PCR-based techniques according to the invention include techniques such as, but not limited to, quantitative PCR (Q-PCR), reverse-transcriptase polymerase chain reaction (RT-PCR), quantitative reverse-transcriptase PCR (QRT-PCR), or digital PCR. These techniques are well known and easily available technologies for those skilled in the art and do not need a precise description.

In some embodiments the determination of viral load is performed by quantitative PCR.

In some embodiments the determination of the viral load is performed by digital PCR. Digital PCR involves multiple PCR analyses on extremely dilute nucleic acids such that most positive amplifications reflect the signal from a single template molecule. Digital PCR thereby permits the counting of individual template molecules. The proportion of positive amplifications among the total number of PCRs analyzed allows an estimation of the template concentration in the original or non-diluted sample. This technique has been proposed to allow the detection of a variety of genetic phenomena (Vogelstein et al., Proc Natl Acad Sci USA 96: 9236-924, 1999). Since template molecule quantification by digital PCR does not rely on dose-response relationships between reporter dyes and nucleic acid concentrations, its analytical precision is, at least theoretically, superior to that of real-time PCR. Hence, digital PCR potentially allows the discrimination of finer degrees of quantitative differences between target and reference loci.

The primers are chosen by the person skilled in the art depending on the desired specificity of the PCR amplification step using standard parameters such as the nucleic acid size, GC contents, and temperature reactions.

The invention further encompasses a PCR or other amplified nucleic acid product comprising an HPV nucleic acid sequence. The amplified product can comprise any of the HPV nucleic acid sequences described herein. In some embodiments the amplification products are amplified using a biological sample containing an HPV nucleic acid. These products can be generated using the techniques set forth in the examples or other techniques known to the skilled artisan. The method can further comprising treating the patient with an anti-HPV treatment or anti-HPV drug, preferably, cidofovir, and subsequently providing a second cell sample from the OLP patient and repeating the step of detecting the presence or absence of a human papilloma virus.

The method can comprise treating an OLP patient with a steroid treatment, immunosuppressant treatment, or photochemotherapy, providing a cell sample from the OLP patient and detecting the presence or absence of a human papilloma virus.

The method can comprise treating an HPV positive oral lichen planus patient with a suitable treatment. In some embodiments the treatment is by a method comprising administering a composition comprising at least one early and/or at least one late protein of an HPV virus, or a fragment thereof. The method can comprise treating an HPV positive oral lichen planus patient with a treatment comprising administering a composition comprising the major capsid protein L1 of HPV types 6, 11, 16, and 18. The method can comprise treating an HPV positive oral lichen planus patient with a treatment comprising administering a composition comprising the major capsid protein L1 of HPV types 16, and 18. The method can comprise treating an HPV positive oral lichen planus patient with a treatment comprising administering a composition comprising at least one chimeric recombinant *Bordetella* sp. adenylate cyclase (CyaA) protein or fragment thereof. In some embodiments the CyaA protein or fragment thereof comprises at least one inserted human papilloma virus (HPV) E6 and/or E7 epitope. Additional treatments are disclosed, for example, in Hung et al., Expert Opin Biol Ther. 2008 April; 8(4): 421-439.

The method can comprise treating an HPV positive oral lichen planus patient with a treatment comprising administering a composition comprising a live-vector based vaccine. For example, the live-vector based vaccine may be a bacterial vector-based vaccine, such as *Salmonella typhimurium* or *Listeria monocytogenes*, or a viral vector-based vaccine, such as adenovirus (AdV).

The method can comprise treating an HPV positive oral lichen planus patient with a treatment comprising administering a composition comprising a peptide and/or protein based vaccine. In preclinical studies, progress has been achieved in augmenting peptide vaccine potency by employing the intranasal route of administration, linking peptides to immunostimulatory molecules to generate protective immunity and specific CTL responses and using DC-activating agents such as 4'-monophosphoryl lipid A (MPL) and GM-CSF to increase and sustain levels of CTL responses. Combining peptides with CpG oligodeoxynucleotide (CpG ODN), which provides a 'danger signal' for Toll-like receptor 9 by mimicking bacterial DNA, has also been shown to enhance the immunogenicity of peptide vaccines. Protein-based vaccination can circumvent the limited specificity of MHC responses associated with some peptide-based vaccines. Various protein vaccines have moved to clinical trials. Fusion proteins containing HPV capsid proteins and HPV early proteins can potentially induce prophylactic and therapeutic immune responses. One example of this experimental fusion vaccine is TA-GW, a fusion of HPV-6 L2 and E7 absorbed onto Alhydrogel. It has been well tolerated by patients in two clinical trials and was effective in clearing HPV genital warts in a subset of patients. A vaccine containing an HPV-16 E6/E7 fusion protein mixed with the ISCOMATRIX adjuvant has also recently been tested in a Phase I study. Immunization with this protein-based vaccine was shown to be safe and immunogenic and resulted in significantly enhanced CD8+ T cell responses to both E6 and E7 in vaccinated patients compared with those observed in placebo recipients. Another protein vaccine, TA-CIN, a fusion of HPV-16 L2, E6 and E7, induced antibodies in all the women tested and induced T cell immunity in a subset of them, proving to be safe. A vaccine termed PD-E7, comprised of mutated HPV-16 E7 fused with a fragment of *Haemophilus influenzae* protein D and formulated in the GlaxoSmithKline Biologicals adjuvant AS02B, has been evaluated in Phase I/II clinical trials and was shown to induce significant E7-specific CTL responses in patients with CIN-1 and CIN-3 lesions. Recently, a fusion of HPV-16 E7 and *M. bovis* hsp65 has been shown to be well tolerated in patients with high-grade anal intraepithelial neoplasia (AIN); however, further tests are needed to determine the clinical efficacy of the vaccine. A recent trial employing the same vaccine was conducted in women with CIN III lesions.

The method can comprise treating an HPV positive oral lichen planus patient with a treatment comprising administering a composition comprising a DNA-based vaccine DNA vaccines have emerged as an attractive and potentially effective strategy for antigen-specific immunotherapy. Naked DNA is safe, stable, relatively easy to manufacture and can be used to sustain the expression of antigen in cells for longer periods of time than RNA or protein vaccines. Furthermore, unlike live-vector vaccines, DNA vaccines do not elicit neutralizing antibody production in the patient, and thus can be repeatedly administered to the same patient effectively.

The method can comprise treating an HPV positive oral lichen planus patient with a treatment comprising administering a composition comprising an RNA replicon-based vaccine. Use of RNA replicons is a relatively new and potentially interesting strategy for HPV vaccination. RNA replicons are naked RNA molecules that replicate within transfected cells. They may be derived from alphaviruses, such as Sindbis virus, Semliki Forest virus, and VEE.

In some embodiments the treated patient is infected with a high risk HPV virus. In some embodiments the treated patient is infected with a human papilloma virus is of a type selected from types 16, 18, 31, 33, 35, 39, 45, 51, 52, 56, 58, 59, 68, 69, 73, and 82.

Anti-HPV Treatment or Anti-HPV Drug

The method can further comprise treating the patient with an anti-HPV treatment or anti-HPV drug. Within the context of the invention, an anti-HPV treatment or anti-HPV drug includes HPV vaccines, cytotoxic agents, immunomodulators, and an antiviral compounds. Subsequently, a second cell sample can be provided from the OLP patient for further determinations.

The method can comprise treating the patient with an HPV vaccine, preferably a therapeutic vaccine. The vaccine can be a peptide-based vaccine, a protein-based vaccine, a live vector-based vaccine, a whole cell-based vaccine or a DNA vaccine. Barrios et al., Cancer Immunol Immunother. 2012 August, 61(8):1307-17; Lin et al., Immunol Res. 2010 July, 47(1-3): 86-112; Li et al., Oncology Reports 24: 1323-1329, 2010; Preville et al., Cancer Res 2005; 65:641-649; Zanotto et al. Journal of Translational Medicine 2011, 9:190; Hung et al., Expert Opin Biol Ther. 2008 April; 8(4): 421-439.

The two currently, FDA-approved prophylactic HPV vaccines are manufactured by Merck (Gardasil®) and GlaxoSmithKline (Cervarix®). Lowy et al., Cancer Prev Res (Phila). 2012 January, 5(1): 18-23. They are non-infectious subunit vaccines produced by expressing the viral L1 major capsid protein in yeast (for the Merck vaccine) or insect cells (for the GSK vaccine). Id. GSK's vaccine is bivalent, being composed of VLPs from HPV16 and -18. Merck's vaccine is a quadrivalent, being composed of VLPs from HPV6, -11, -16, and -18. Id.

Exemplary therapeutic vaccines are known in the art. For example, therapeutic vaccines are disclosed in U.S. Pat. Nos. 8,628,779 and 8,637,039. In some embodiments the therapeutic vaccine comprises at least one chimeric recombinant *Bordetella* sp. adenylate cyclase (CyaA) protein or fragment thereof, the CyaA protein or fragment thereof comprising at least one inserted human papilloma virus (HPV) E7 epitope. In some embodiments the chimeric recombinant CyaA protein or fragment thereof retains the property of the CyaA protein to target CD11b/CD18 Antigen Presenting Cells (APC). In some embodiments the chimeric recombinant CyaA protein or fragment thereof retains the property of the CyaA protein to cause translocation of the at least one inserted HPV E7 epitope into the cytosol of targeted cells in the subject. In some embodiments the at least one inserted HPV E7 epitope is from a high risk HPV type. In some embodiments the at least one inserted HPV E7 epitope is from an HPV type selected from types 16, 18, 31, 33, 35, 39, 45, 51, 52, 56, 58, 59, 68, 69, 73, and 82. In some embodiments the at least one inserted HPV E7 epitope is from HPV16. In some embodiments the at least one inserted HPV E7 epitope is from HPV 18. In some embodiments the chimeric recombinant CyaA protein or fragment thereof comprises from about 30 to about 1300 amino acid residues of the CyaA protein, wherein the about 30 to about 1300 amino acid residues comprise at least one fragment selected from amino acid residues 1208 to 1243 of the CyaA protein of *Bordetella pertussis* and amino acid residues 1188 to 1281 of the CyaA protein of *Bordetella pertussis*. In some embodiments the chimeric recombinant CyaA protein or fragment thereof does not comprise amino acid residues 225 to 234 of the CyaA protein. In some embodiments the chimeric recombinant CyaA protein or fragment thereof comprises an inserted polypeptide comprising from about 5 to about 500 amino acid residues that comprises the at least one inserted HPV E7 epitope. In some embodiments the chimeric recombinant CyaA protein or fragment thereof comprises an inserted polypeptide comprising from about 5 to about 200 amino acid residues that comprises the at least one inserted HPV E7 epitope. In some embodiments the chimeric recombinant CyaA protein or fragment thereof comprises an inserted polypeptide comprising from about 10 to about 50 amino acid residues that comprises the at least one inserted HPV E7 epitope. In some embodiments the chimeric recombinant CyaA protein or fragment thereof is obtained by insertion of at least two fragments of the native E7 protein in at least two permissive sites of the CyaA protein or fragment thereof, wherein the orientation of the at least two inserted fragments is reversed with respect to their natural location in the E7 protein. In some embodiments the chimeric recombinant CyaA protein or fragment thereof comprises an inserted polypeptide comprising residues 1 to 29 of the E7 protein of HPV16, or comprising residues 43 to 98 of E7 protein of HPV16, or both fragments inserted in different permissive sites. In some embodiments the chimeric recombinant CyaA protein or fragment thereof comprises an inserted polypeptide comprising at least one sequence selected from amino acid sequence RAHYNIVTF (SEQ ID NO: 27) ($E7_{49-57}$) and amino acid sequence GQAEPDRAHYNIVTFCCKCDSTLRLCVQSTHVDIR (SEQ ID NO: 30) ($E7_{43-77}$). In some embodiments the CyaA protein or fragment thereof is the *Bordetella pertussis* CyaA protein or a fragment thereof. In some embodiments the enzymatic activity of the CyaA protein or fragment thereof has been inactivated. In some embodiments the enzymatic activity of the CyaA protein or fragment thereof has been genetically inactivated. In some embodiments the enzymatic activity of the CyaA protein or fragment thereof has been genetically inactivated as a result of a dipeptide inserted in a site of the amino acid sequence of CyaA involved in cyclase activity. In some embodiments the dipeptide is inserted into the CyaA protein or fragment thereof between residues 188 and 189 of the native CyaA protein. In some embodiments the chimeric recombinant CyaA protein is encoded by the insert contained in plasmid pTRACE5-HPV16E7$_{FULL}$ (C.N.C.M. 1-3191). In some embodiments the chimeric recombinant CyaA protein is encoded by the insert contained in plasmid pTRACE5-HPV16E7$_{\Delta 30\_42}$ (C.N.C.M. 1-3190). In some embodiments the vaccine composition elicits a cell-mediated immune response when administered to a mammalian subject. In some embodiments the vaccine composition elicits a humoral immune response when administered to a mammalian subject. In some embodiments the vaccine composition further comprises at least one of a physiologically acceptable vehicle, a physiologically acceptable excipient, a physiologically acceptable carrier, and a physiologically acceptable diluent. In some embodiments the vaccine composition further comprises at least one of an adjuvant, a surfactant, and an immunomodulating substance. In some embodiments the chimeric recombinant CyaA protein or fragment thereof comprises at least two E7 epitopes inserted in different permissive sites. In some embodiments the at least two inserted E7 epitopes are a fragment of the E7 protein of HPV 16 and a fragment of the E7 protein of HPV18. In some embodiments the at least two inserted E7 epitopes are fragments of the E7 protein of HPV 16. In some embodiments the at least two inserted E7 epitopes are fragments of the E7 protein of HPV18. In some embodiments at least one of the fragments of the E7 protein of HPV 16 is selected from a fragment comprising the first 29 amino acid residues of HPV 16-E7 inserted into the CyaA protein or fragment thereof between residues 319 and 320 of the native CyaA protein and a fragment comprising amino acid residues 43 to 98 of HPV16-E7 inserted into the CyaA protein or fragment thereof between residues 224 and 235 of the native CyaA protein. In some embodiments the chimeric recombinant CyaA protein or fragment thereof comprises the fragment comprising the first 29 amino acid residues of HPV16-E7 inserted between residues 319 and 320 of the native CyaA protein and the fragment comprising amino acid residues 43 to 98 of HPV16-E7 inserted between residues 224 and 235 of the native CyaA protein. In some embodiments at least one of the fragments of the E7 protein of HPV18 is selected from a fragment comprising the first 31 amino acid residues of HPV18-E7 inserted into the CyaA protein or fragment thereof between residues 319 and 320 of the native CyaA protein and a fragment comprising amino acid residues 43 to 105 of HPV 18-E7 inserted into the CyaA protein or fragment thereof between residues 224 and 235 of the native CyaA protein. In some embodiments the CyaA protein or fragment thereof comprises the fragment comprising the first 31 amino acid residues of HPV18-E7 inserted between residues 319 and 320 of the native CyaA protein and the fragment comprising amino acid residues 43 to 105 of HPV 18-E7 inserted between residues 224 and 235 of the native CyaA protein. In some embodiments the composition comprises at least two different chimeric recombinant CyaA proteins or fragments thereof. In some embodiments the first of the at least two chimeric recombinant CyaA proteins or fragments thereof comprises a fragment of the E7 protein of HPV16 selected from a fragment comprising the first 29 amino acid residues of HPV16-E7 inserted between residues 319 and 320 of the native CyaA protein and a fragment comprising amino acid residues 43 to 98 of HPV16-E7 inserted between residues 224 and 235 of the native CyaA protein; and wherein the second of the at least two chimeric recombinant CyaA proteins or fragments thereof comprises a fragment of the E7 protein of HPV18 selected from a fragment comprising the first 31 amino acid residues of HPV18-E7 inserted between residues 319 and 320 of the native CyaA protein and a fragment comprising amino acid residues 43 to 105 of HPV 18-E7 inserted between residues 224 and 235 of the native CyaA protein. In some embodiments the first of the at least two CyaA proteins or fragments thereof comprises the fragment comprising the first 29 amino acid residues of HPV16-E7 inserted between residues 319 and 320 of the native CyaA protein and comprises the fragment comprising amino acid residues 43 to 98 of HPV16-E7 inserted between residues 224 and 235 of the native CyaA protein; and wherein the second of the at least two CyaA proteins or fragments thereof comprises the fragment comprising first 31 amino acid residues of HPV18-E7 inserted between residues 319 and 320 of the native CyaA protein and the fragment comprising amino acid residues 43 to 105 of HPV 18-E7 inserted between residues 224 and 235 of the native CyaA protein. In some embodiments the chimeric recombinant CyaA protein or fragment thereof comprises residues 43 to 98 of HPV16-E7 followed by residues 43 to 105 of HPV18-E7 inserted between residues 224 and 235 of the native CyaA protein and the first 31 amino acid residues of HPV18-E7 followed by the first 29 amino acid residues of HPV16-E7 inserted between residues 319 and 320 of the native CyaA protein. In some embodiments the CyaA protein or fragment thereof is enzymatically inactivated by insertion of a LQ dipeptide between amino acid residues Asp 188 and Ile 189 of the native CyaA protein. In some embodiments the at least one inserted HPV E7 epitope has been modified with respect to its native amino acid sequence by addition of non-naturally flanking sequences. The method can comprise treating the patient with a cytotoxic agent. Cytotoxic agents include Podophyllotoxin and Trichloracetic acid.

The method can comprise treating the patient with an immunomodulator. Immunomodulators include imiquimod and cidofovir.

The method can comprise treating the patient with an antiviral compound. Antiviral compounds include small molecule inhibitors. In one embodiment, compounds PFL #13 or #14 of Huang et al., Antiviral Res. 2012 February, 93(2): 280-287, can be used. In one embodiment, compounds #1, 2, or 3 of White et al., J. Biol. Chem. 2003, 278:26765-26772, can be used. Their structures are incorporated herein by reference.

Thus, the present invention also relates to an anti-HPV treatment or anti-HPV drug as described herein for use in any one of the herein-disclosed methods.

Methods for Detecting a Reduction in an Oral Lichen Planus Symptom

The invention includes methods comprising a step of detecting a reduction in an OLP symptom. The primary lesion of OLP is a small opalescent papule, whitish and keratotic (not removable with a spatula). Nico et al., An Bras Dermatol. 2011; 86(4):633-43. In the erosive form, bright red well-demarcated erosions are observed, characteristically surrounded by typical papulae. Id. Pain is usually intense. Id. The detection of a reduction in an OLP symptom can be performed using standard clinical criteria.

Methods for Monitoring Treatment of an Oral Lichen Planus Patient

The invention includes methods for monitoring treatment of an OLP patient. These methods can comprise treating an OLP patient with an anti-HPV treatment or a steroid treatment, immunosuppressant treatment, or photochemotherapy and determining whether the treatment has decreased an HPV-induced immune response, preferably a T-cell response, against a human papilloma virus infection in the cell sample. These methods can comprise treating an OLP patient with an anti-HPV treatment and determining whether the treatment has decreased an OLP symptom in the patient.

Methods and Compositions for Use in the Treatment of Oral Lichen Planus

The invention encompasses methods and compositions for use in treating an OLP patient.

In one embodiment, the method comprises specifically immunotargeting subsets of T cells. In one embodiment, the method comprises immunotargeting of the CD8+ TCRVβ3+ population in order to delete or anergise this subset. In one embodiment, a monoclonal antibody or other cell binding domain can be spliced to a toxin domain. Knechtle, Phil. Trans. R. Soc. Lond (2001) 356, 681-689.

In one embodiment, anti-TCRVβ3 monoclonal antibodies are used. In one embodiment, bispecific CD8/Vβ3 immunoreactants are used.

In one embodiment, the method comprises immunotargeting of the CD8+ TCRVß3+Jß2.7 population in order to delete or anergise this subset. In one embodiment, the specific sequence SEPGQGFGEQ (SEQ ID NO:2) is targeted in order to delete or anergise this subset. In one embodiment, a monoclonal antibody against any of SEQ ID NOs: 1-10 is spliced to a toxin domain in order to delete or anergise this subset.

In one embodiment, the method comprises immunotargeting of the CD8+ TCRVß3+HPV+ population. In one embodiment, an HPV-specific multimer, preferably an HPV16-specific multimer coupled to a toxin, is used to delete or anergise this subset. See, e.g., Gojanovich et al., Journal of Diabetes Science and Technology Volume 6, Issue 3, May 2012; Vincent et al., J Immunol 2010, 184:4196-4204, which are hereby incorporated by reference. In one embodiment, the HPV 16-specific multimer comprises at least one amino acid sequence selected from SEQ ID NOs:21-29.

Preferably, the toxin is doxorubicin or saporin.

In one embodiment, the method comprises treating the patient with (i) an anti-HPV treatment or anti-HPV drug or (ii) a steroid treatment, immunosuppressant treatment, or extracorporeal photochemotherapy. In one embodiment, the method comprises treating the patient with (i) an anti-HPV treatment or anti-HPV drug and (ii) a steroid treatment, immunosuppressant treatment, or photochemotherapy. Preferably, the patient is treated with extracorporeal photochemotherapy. Preferably, the anti-HPV treatment or anti-HPV drug is cidofovir.

In one embodiment, the method further comprises detecting the presence of a human papilloma virus or an immune response against a human papilloma virus infection in a cell sample from the patient. Any of the assays described herein or known to the skilled artisan can be used.

The invention comprises the use of any of the above compounds for the treatment of oral lichen planus and the use of any of the above compounds for the preparation of a medicament for treating an OLP patient. The invention further comprises any of the above compounds for use in the treatment of OLP. The invention further comprises any of the above compounds for use in the prevention of severe erosive OLP.

The invention also encompasses methods for treating an oral lichen planus patient comprising selecting an HPV positive oral lichen planus patient and treating the HPV positive oral lichen planus patient. As shown in the examples, one way that such patients may be treated is by a method that comprises extracorporeal photochemotherapy (ECP). Accordingly, the invention also encompasses a method for treating an oral lichen planus patient comprising selecting an HPV positive oral lichen planus patient; and treating the HPV positive oral lichen planus patient with extracorporeal photochemotherapy (ECP). The patient can be HPV16 positive. In one embodiment, selecting an HPV positive oral lichen planus patient comprises detecting the presence of a human papilloma virus or an immune response against a human papilloma virus infection in a cell sample from the patient. Any of the assays described herein or known to the skilled artisan can be used.

The invention also encompasses methods for treating an oral lichen planus patient comprising selecting an oral lichen planus patient infected with a high risk strain of HPV and treating the high risk HPV positive oral lichen planus patient. In some embodiments the high risk strain is selected from HPV types 16, 18, 31, 33, 35, 39, 45, 51, 52, 56, 58, 59, 68, 69, 73, and 82. In some embodiments the patient is a patient with a persistent high risk HPV infection. In some embodiments the treatment prevents oral lichen planus in the patient, and particularly severe erosive form of oral lichen planus. In some embodiments, the treatment ameliorates oral lichen planus in the patient.

The method can comprise treating an HPV positive oral lichen planus patient with a treatment selected from a composition comprising the major capsid protein L1 of HPV types 6, 11, 16, and 18; a composition comprising the major capsid protein L1 of HPV types 16, and 18; and at least one chimeric recombinant *Bordetella* sp. adenylate cyclase (CyaA) protein or fragment thereof, the CyaA protein or fragment thereof comprising at least one inserted human papilloma virus (HPV) E7 epitope. In some embodiments the human papilloma virus is a high risk HPV virus. In some embodiments the human papilloma virus is of a type selected from types 16, 18, 31, 33, 35, 39, 45, 51, 52, 56, 58, 59, 68, 69, 73, and 82.

The invention further encompasses the embodiments set forth in the examples and combinations of them with the embodiments disclosed herein.

EXAMPLES

Example 1. Patients and Healthy Donors

Ten patients with severe erosive OLP treated with ECP between 1995 and 2009 were enrolled in this study. They consisted of 8 women and 2 men, with a mean age of 56.5 years (range: 25-78). The main characteristics of 8 of these patients have been previously reported. Additional data are listed in FIG. 6. Previous treatment with topical or systemic glucocorticoids and immunosuppressive agents was considered insufficiently effective on their disease. Glucocorticoids and immunosuppressive treatments were stopped at least 4 weeks before ECP initiation. All patients reached remission under ACP, which was complete (CR) in six, and partial (PR, defined by regression of lesions of at least 50%) in four of them, as previously described. The patient clinical status was determined at the time of collection of each blood sample, which was then stored for further analysis. The Institutional Review Board (Comite de Protection des Personnes Ile de France IV, 2009/10NI) approved the study. Healthy donors (HD) were blood donors from the Etablissement Français du Sang.

Example 2. Preparation of Peripheral Blood Mononuclear Cells

Peripheral blood was collected at baseline before any ECP treatment ('flare') and at the time of maximal clinical response (complete or partial). PBMCs were prepared by Ficoll-Hypaque density gradient centrifugation, and cryopreserved in liquid nitrogen in 8% dimethylsulfoxide (DMSO), 42% fetal calf serum, and 50% RPMI-1640 medium (Invitrogen).

Example 3. Antibodies and Flow Cytometric Analysis

The following reagents were used: anti-CD3 FITC (Clone BW264/56, Miltenyi Biotec), anti-CD8-APC (SK1, BD Pharmingen), Dextramer-HPV E7$_{11-20}$-PE (Dext-HPV PE) (HLA-A*0201; YMLDLQPETT, Immudex), Dextramer-HIV-1 P17 Gag 77-85-PE (Dext-HIV-PE)(HLA-A*0201; SLYNTVATL, Immudex), anti-TCR-Vβ3-FITC (JOVI-3, Ancell). Cells were incubated with Dext as recommended by the manufacturer for 10 min at room temperature, then mAb were added for 30 min at 4° C. Stained cells were washed with PBS/0.5% BSA/0.1% NaN3 (PBA), and were analyzed using a FACSCalibur flow cytometer (Becton Dickinson).

Example 4. Purification of T-Lymphocyte Subsets

PBMCs were thawed at 37° C., resuspended in complete medium (RPMI 1640 with 10% fetal calf serum supplemented with L-glutamine, and penicillin-streptomycin), washed with cold PBS then stabilized in PrepProtect buffer. Dead cells were removed using the MACS® Dead Cell Removal kit. CD8+ and CD4+ T-cells were isolated using anti-CD8 or anti-CD4 Ab-coated immunomagnetic beads and stabilized in PrepProtect buffer according to manufacturer's instructions (Miltenyi Biotec). Cell purities exceeded 85%. CD3+CD8+ TCRVβ3+ Dext-HPV+ or Dext-HPV− populations were isolated using a MoFlo® Astrios™ cytometer cell sorter (Beckman Coulter, Villepinte, France). Sorted cell subsets were recovered in buffer RLT (Qiagen) for RNA extraction.

Example 5. T-Cell Receptor Repertoire Analysis

RNA from cells was extracted using RNAeasy kit (Qiagen) and reverse-transcribed into cDNA using Superscript II (Invitrogen Life Technologies). Quantitative PCR amplifications were performed as described elsewhere (Fazilleau N, Bachelez H, Gougeon M L, Viguier M. Cutting edge: size and diversity of CD4+CD25high Foxp3+ regulatory T cell repertoire in humans: evidence for similarities and partial overlapping with CD4+CD25-T cells. J Immunol 2007; 179:3412-6) with TaqMan Universal PCR Master Mix (Applied Biosystems), TCRVβ gene segments specific oligonucleotides, TCRCβ-specific antisense primer and a fluorescent probe specific for the TCRCβ gene segment.

Example 6. Cloning and Sequencing of CDR3β Rearrangements

Vβ-Jβ PCR products were cloned in pCR®4Blunt TOPO vector (Invitrogen Life Technologies). Sequencing reactions were performed using the ABI PRISM Big Dye Terminator Reaction Kit (Applied Biosystem). Reaction products were analyzed on an ABI 3130XL 16 capillaries (Applied Biosystems.

Example 7. Detection of Human Papilloma Virus Subtypes

Lichen skin and/or mucous membranes samples were obtained either atraumatically using a cytobrush (DNAPAP Cervical Sampler; Digene), secondarily placed in Cervical Specimen Transport Medium (Digene) or either by tissue biopsy secondarily frozen. DNA extraction was performed using the QIAGEN BioRobot EZ1 with the EZ1 DNA Tissue Kit (QIAGEN). Detection of HPV was performed using a type-specific multiplex genotyping assay as described elsewhere (Ruer J B, Pepin L, Gheit T, et al. Detection of alpha- and beta-human papillomavirus (HPV) in cutaneous melanoma: a matched and controlled study using specific multiplex PCR combined with DNA microarray primer extension. Experimental dermatology 2009; 18:857-62). The assay detects HPV DNA of 19 mucosal high-risk and potential high-risk HPV types (16, 18, 26, 31, 33, 35, 39, 45, 51, 52, 53, 56, 58, 59, 66, 68, 70, 73, 82), 2 mucosal low-risk HPV types (6, 11), 25 cutaneous HPV types from genus 0 (5, 8, 9, 12, 14, 15, 17, 19, 20, 21, 22, 23, 24, 25, 36, 37, 38, 47, 49, 75, 76, 80, 92, 93, 96), 16 genus-Gamma types (4, 65, 95, 60, 48, 50, 88, 101, 103, 108, 109, 112, 116, 119, 121, and 123), 5 genus-alpha HPV types (2, 3, 10, 27, and 57), and the single type in genus-mu (1). Search for serum IgG antibodies against HPV 16 major capsid protein L1 was performed using enzyme-linked immunosorbent assay (ELISA), as previously described (Combita A L, Bravo M M, Touze A, Orozco O, Coursaget P. Serologic response to human oncogenic papillomavirus types 16, 18, 31, 33, 39, 58 and 59 virus-like particles in colombian women with invasive cervical cancer. Int J Cancer 2002; 97:796-803).

Example 8. In Situ Immunostainings

Surface expression in lesional tissue was assessed on 4-μm thick paraffin sections using automated indirect immunoperoxidase staining (Benchmark XT; Ventana). Anti-human CD3 Ab, anti-human CD8 Ab (clone C8/144B) (Dako, Glostrup) and anti-human TIA-1 Ab (clone 2G9A10F5, Beckman-Coulter) were used as the primary antibodies. Acetone-fixed cryosections were incubated with Dext-HPV or Dext-HIV PE for 75 minutes at room temperature in the dark, rinsed in PBS, and mounted with VECTASHIELD® Mounting Medium with DAPI (Vector Laboratories). Slides were studied using an Axiovert 200M microscope with MRm camera (Zeiss).

Example 9. Statistical Analysis

Unpaired t-tests were calculated using Prism software.

Example 10. TCRVβ3+ Clonal Expansions Alter CD8+ T-Cell Repertoires of OLP Patients at Flare To understand the molecular events that govern the physiopathology of OLP, the T-cell Repertoire of 10 patients with OLP was investigated. At flare, the usage of each TCRVβ gene segment, as estimated by RT-qPCR in CD4+ and CD8+ peripheral blood T-cells, revealed striking predominance of the TCRVβ3 gene segment in CD8+ T-cells (26.49%±4.81), while it was used at a much lower level in the circulating CD4+ counterparts (11.49%±2.24) or in both isolated CD4+ and CD8+ T-cells from HD (FIG. 1a). Results from RT-qPCR were confirmed by flow cytometry, showing predominance of TCRVβ3 expression in the peripheral blood CD8+ T-lymphocytes of 7 of the 10 patients (data not shown, 17.27%±4.51).

The qPCR products were further used as a matrix for the amplification of dye-labeled oligonucleotides specific for Cβ and allowed to assess the complementary determining region 3 (CDR3) length distribution. For each TCRVβ gene segment tested (data not shown) and for the TCRVβ3 gene segment from CD4+ and CD8+ T-cells from HD or from CD4+ T-cells isolated from OLP patients (FIG. 1b), CDR3β length distribution profiles displayed Gaussian-like curves, the hallmark of a polyclonal T-cell repertoire. In contrast, CDR3β distribution profiles of the TCRVβ3 gene segment were altered with single expansions in blood CD8+ T-cells from all OLP patients, as shown in OLP#5 showing a peak with a CDR3β size of 11 AA (FIG. 1b). Therefore, for each OLP patient, the Vβ-Jβ rearrangement corresponding to the observed clonal expansion was determined, cloned, and sequenced. As shown in FIG. 1c, one single CDR3β sequence was found in each patient. Further, all TCRVβ3+ clonal expansions were also present in tissue lesions of 3 different OLP patients (FIG. 1d). Overall, neither CDR3β length nor consensus sequence could be found among all OLP patients but strikingly all detected CD8+ clonal expansions were using the TCRVβ3 gene segment, even in patients not sharing common class I HLA alleles (FIG. 6). Surprisingly, it was also found that 5 out of the 10 clonotypic TCR were composed of the Vβ3-Jb2.7 rearrangement and that one clonotypic sequence was found in two different patients (OLP#2, #8). Of note, flow cytometry characterization of TCRVβ3+CD8+ T-cells in PBMCs confirmed their activated status as shown by surface expression of HLA-DR (data not shown, 20.99%±4.52, n=7), CD38 (24.85%±6.18, n=4) and perforin (15.20%±4.54, n=7). Altogether, these data show that clonotypic TCRVβ3+CD8+ T-cell expansions are detected in situ and in the blood of OLP patients at flare.

Figure 2:
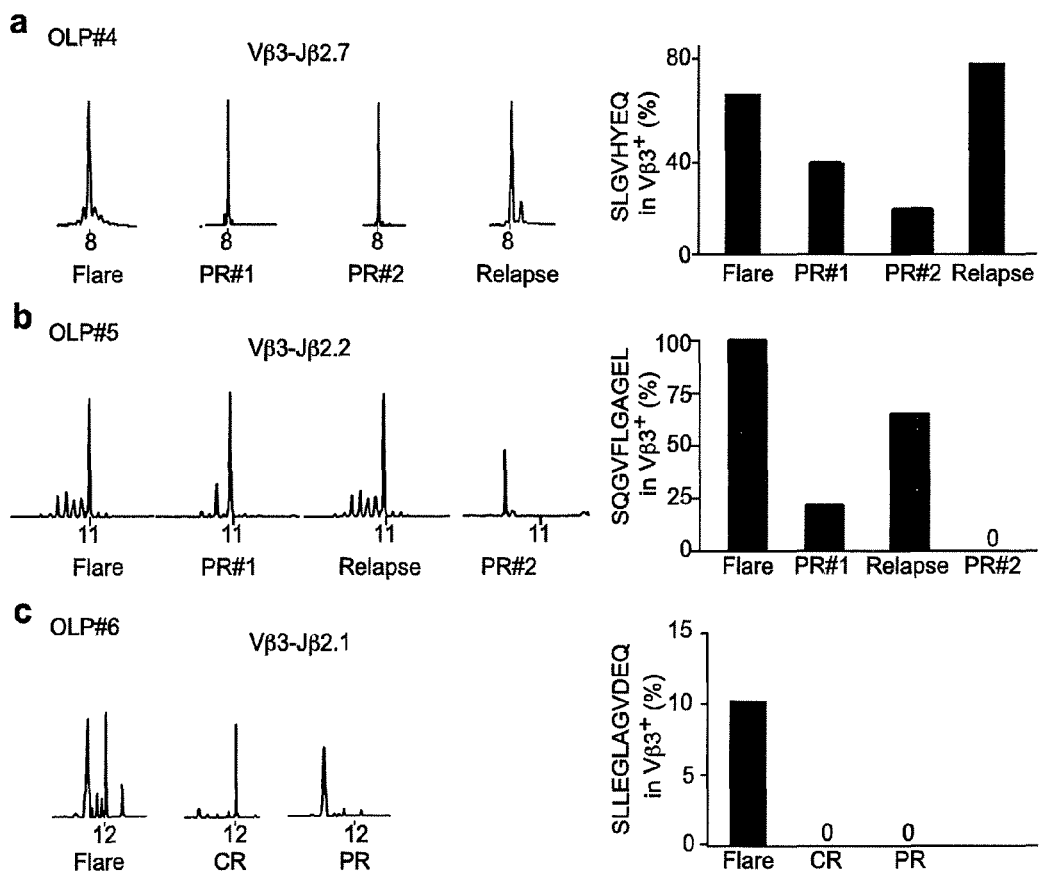
FIGS. 2a-c depict TCRVβ3+ clonal expansions over the course of the disease in OLP patients. CDR3β length distributions for CD8+ Vβ3-Jβ2.7, Vβ3-Jβ2.2 and Vβ3-Jβ2.1, rearrangements over the course of the disease and clonotype distribution estimated by CDR3 sequencing for OLP#4 (a), OLP#5 (b) and OLP#6 (c), respectively.
Figure 5:
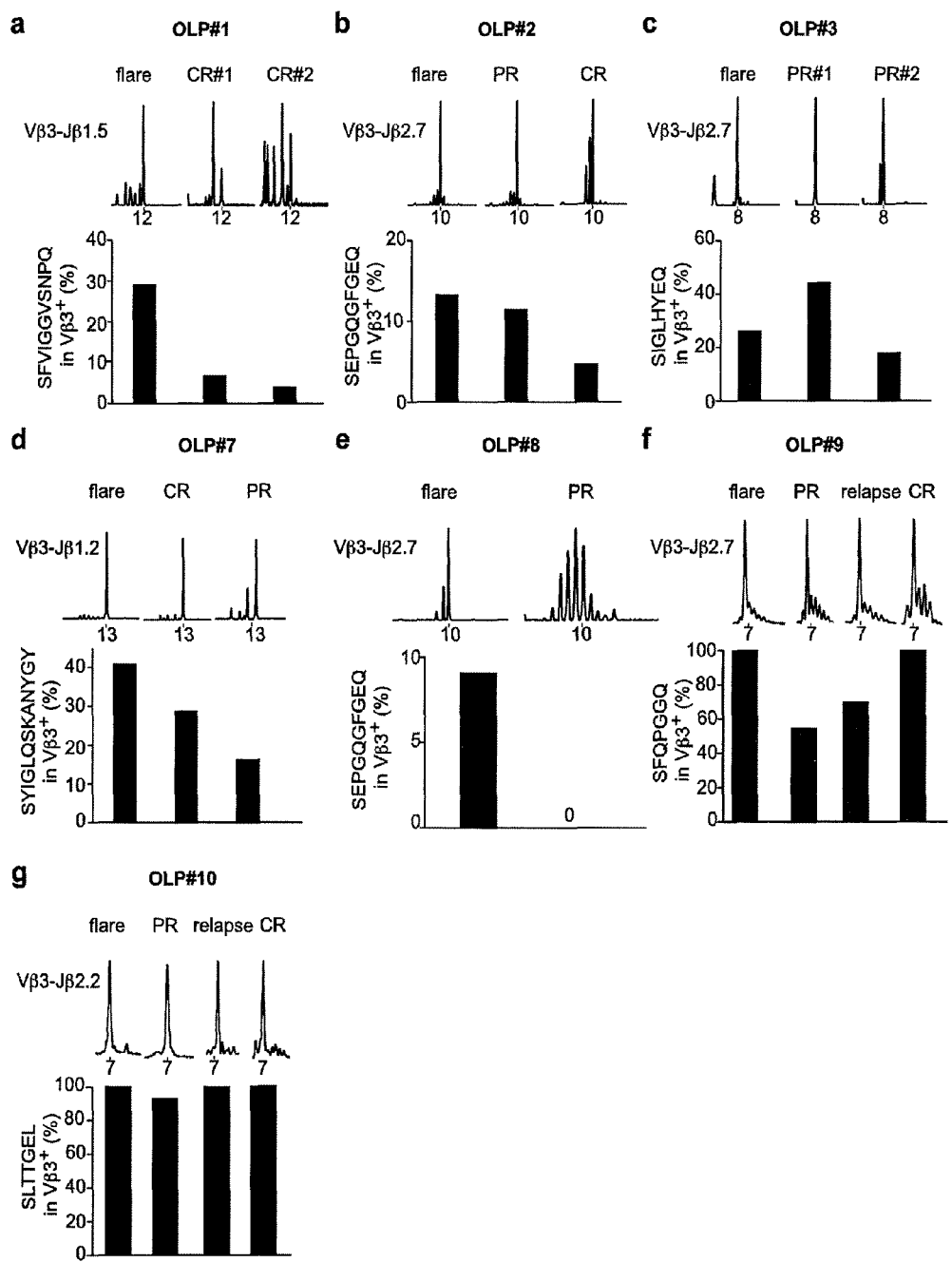
FIGS. 5a-g depict TCRVβ3+ clonal expansions over the course of the disease in OLP patients. CDR3β length distributions for CD8+ Vl3-Jβ1.5, Vβ3-Jβ2.7, Vβ3-Jβ2.7, Vβ3-Jβ1.2, Vβ3-Jβ2.7, Vβ3-Jβ2.7 and Vβ3-Jβ2.2, rearrangements over the course of the disease and clonotype distribution estimated by CDR3 sequencing for OLP#1 (a), OLP#2 (b), OLP#3 (c), OLP#7 (d), OLP#8 (e), OLP#9 (f) and OLP#10 (g) respectively. PR, partial remission; CR, complete remission.

Example 11. Tracking of CD8+ TCRVβ3+ Clonal Expansions During Disease Follow-Up in OLP Patients To determine whether the CD8+ clonal expansions with a distinct TCRVβ3+ could actively participate to the physiopathology of OLP, several approaches were used. First, PBMCs for each OLP patient were isolated at different time points with the clinical status correlation: flare (before starting ECP), partial remission (PR) and/or complete remission (CR) obtained with ECP or relapse after ECP withdrawal (FIG. 2 and FIG. 5). For all collected samples, TCRVβ usage and CDR3β length distribution for each TCRVβ gene segment were performed as well as sequencing of Vβ-Jβ rearrangements corresponding to the clonal expansions at flare as described above (FIG. 1). This allowed a follow-up of peaks corresponding to TCRVβ3+ clonal expansions in the T-cell compartment. For 3 patients (OLP#5, #6 and #8), it was observed a disappearance of the peaks corresponding to the TCRVβ3+ clonal expansions that strikingly correlated with the clinical status (FIG. 2a and FIG. 5). However, for the 7 remaining OLP patients (as an example OLP#4 FIG. 2a), CDR3 distribution profiles were all disturbed irrespective of the clinical status of the patients. Therefore, in order to better estimate the usage of each TCRVβ3+ clonal expansion, the corresponding Vβ-Jβ rearrangement was amplified, cloned and sequenced. A strong correlation between the clonotype usage and the clinical status of OLP patients was found in 8 out of 10. A pronounced decrease or disappearance of the frequency of TCRVβ3+ clonotype was observed in patients OLP#1, #4, #5, #6, #8, while a slight decrease was found in cases OLP#2, #3 and #7 (FIG. 2b and FIG. 5). Moreover, the clonotype identified at initial flare was also found at high frequency at the time of clinical relapse (OLP#4, #5 FIG. 2b and OLP#9, #10 FIG. 5). Overall, these data support that clinical remission obtained with ECP in OLP is associated in most cases with a decrease or disappearance of TCRVβ3 clonotypic CD8+ T-cell expansions.

Example 12. CD8+ T-Cells Expressing Clonal TCRVβ3+ in OLP Patients are Specific for HPV16

Figure 3:
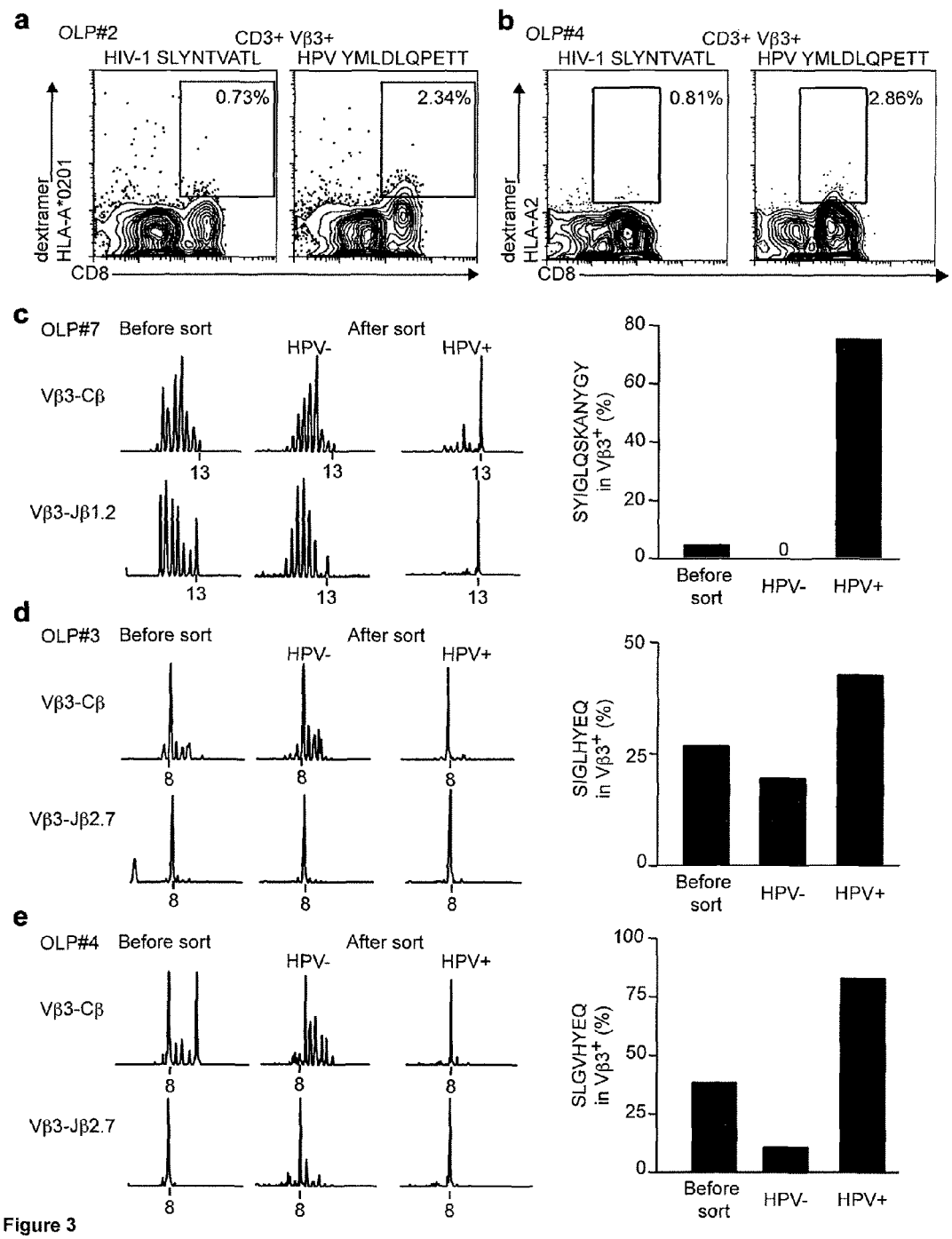
FIGS. 3a-e depict CD8+ T-cells expressing clonal TCRVβ3+ are enriched in HPV16+ population. Flow cytometry contour plots of HIV- and HPV-specific CD8+ T cells in the blood of OLP #2 at flare (a) and OLP#4 during ECP session (b). CDR3β length distributions for Vβ3-Cb and Vβ3-Jβ1.2 rearrangements from OLP#7 HPV− and HPV+ population as well as SYIGLQSKANYGY (SEQ ID NO:7) clonotype distribution estimated by CDR3 sequencing (c). CDR3β length distributions for Vβ3-Cb and Vβ3-Jβ2.7 rearrangements from OLP#3 HPV− and HPV+ population as well as SIGLHYEQ (SEQ ID NO:3) clonotype distribution estimated by CDR3 sequencing (d). CDR3β length distributions for Vβ3-Cb and Vβ3-Jβ2.7 rearrangements from OLP#4 HPV− and HPV+ population as well as SLGVHYEQ (SEQ ID NO:4) clonotype distribution estimated by CDR3 sequencing (e).
Figure 4:
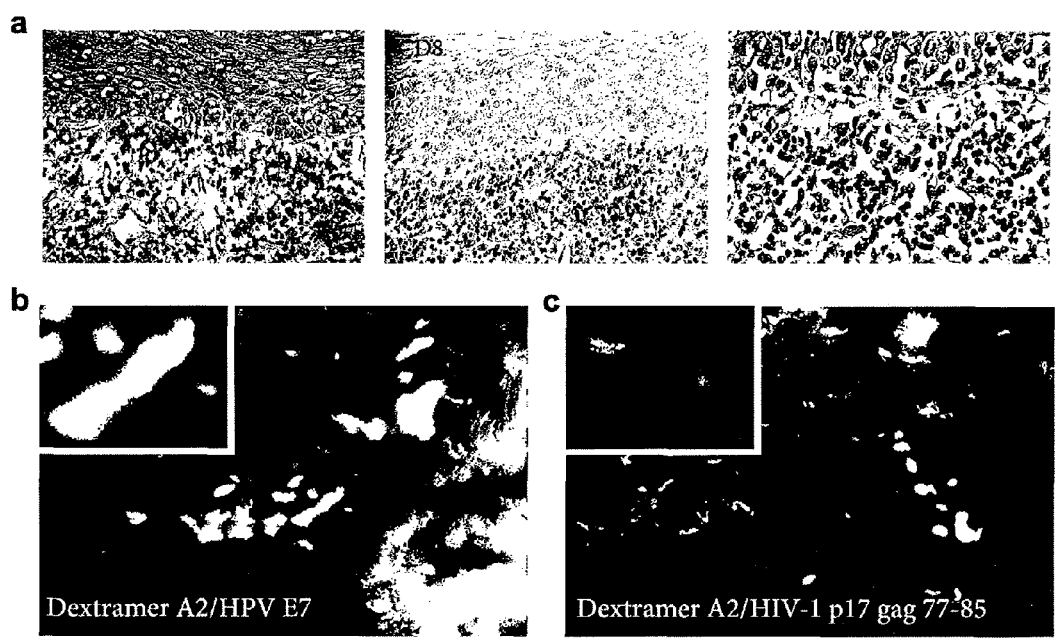
FIGS. 4a-c depict HPV16-specific CD8+ T-cells infiltrate OLP lesions. CD3, CD8 and TIA-1 (T-cell-restricted intracellular antigen 1) expression in a biopsy taken from mucosal lesions in OLP#2, as assessed by immunostaining in situ analysis (a, ×200 (CD3, CD8) or ×400 (TIA-1) magnification). Staining was performed using Dext-HPV PE (b, ×630 magnification, inset ×1000 magnification) and Dext-HIV-PE (c, ×630 magnification, inset ×1000 magnification).

Lesional CTLs from OLP patients are suspected to recognize an Ag associated with MHC class I molecule on lesional keratinocytes (Sugerman P B, Satterwhite K, Bigby M. Autocytotoxic T-cell clones in lichen planus. The British journal of dermatology 2000; 142:449-56), and on another hand several studies have shown the presence of several HPV subtypes, including HPV16 and HPV18, in mucosal OLP lesions (Jontell M, Watts S, Wallstrom M, Levin L, Sloberg K. Human papilloma virus in erosive oral lichen planus. J Oral Pathol Med 1990; 19:273-7; Young S K, Min K W. In situ DNA hybridization analysis of oral papillomas, leukoplakias, and carcinomas for human papillomavirus. Oral surgery, oral medicine, and oral pathology 1991; 71:726-9; Lodi G, Scully C, Carrozzo M, Griffiths M, Sugerman P B, Thongprasom K. Current controversies in oral lichen planus: report of an international consensus meeting. Part 1. Viral infections and etiopathogenesis. Oral Surg Oral Med Oral Pathol Oral Radiol Endod 2005; 100: 40-51; Miller C S, White D K, Royse D D. In situ hybridization analysis of human papillomavirus in orofacial lesions using a consensus biotinylated probe. Am J Dermatopathol 1993; 15:256-9; Yildirim B, Senguven B, Demir C. Prevalence of herpes simplex, Epstein Barr and human papilloma viruses in oral lichen planus. Medicina oral, patologia oral y cirugia bucal 2011; 16:e170-4). Detection of current or past HPV infection could be performed in 6 out of 10 patients either on skin or mucosal biopsy, cytobrush or by serology. Three out of 6 OLP patients in the cohort were found HPV positive and HPV16 DNA and/or IgG against HPV16 were found in 2 out of 6 patients (OLP#2 and OLP#5) (FIG. 6). It was hypothesized that TCRVβ3+ clonal expansions, which usage correlated with OLP clinical activity, might exhibit HPV-specificity. In this attempt, peptide-containing MHC class I dextramer were used to stain PBMCs of all 5 HLA-A*0201+ OLP patients from the cohort. In all these 5 cases a distinct population of CD8+ T-cells expressing a TCRVβ3 specific for the $E7_{11-20}$ immunodominant peptide of HPV 16 was observed, as shown for OLP#2 at flare (FIG. 3a) or OLP#4 under ECP (FIG. 3b) (mean percentage of TCRVβ3+CD3+CD8+ T-cells expressing Dext-HPV: 2.62%±1.7, n=5; Dext-HIV: 0.64%±0.3, n=5). As expected, almost no CD8+ TCRVβ3+ T-cells were stained with HLA-A2/HIV-p17 Gag dextramer in these HIV negative patients (FIG. 3a-b). HPV-specific CD8+ TCRVβ3+ cells were sorted, as well as their CD8+ TCRVβ3+ dextr HPV-counterparts from OLP#3, #4 and #7. Spectratyping analysis, CDR3β sequencing and clonotypic usage studies were performed, revealing a striking enrichment of dextramer HPV+ populations with the clonotype, in contrast with dextramer HPV− subset which showed no enrichment (FIG. 3c-e). In the last series of experiment, in situ immunostaining was performed using HLA-A2/HPV $E7_{11-20}$-specific dextramer on OLP lesion from OLP#2. The presence of cells expressing CD3, CD8 and the cytotoxic marker TIA1 was detected (FIG. 4a), some of these bearing TCR specific for HLA-A2/HPV $E7_{11-20}$ peptide (FIG. 4b), whereas staining with HLA-A2/HIV-p17Gag dextramer yielded negative results in the same patient (FIG. 4c).

Overall, these data demonstrate that a notable proportion of clonal CD8+ blood T-cells of OLP patients are HPV16-specific, and are also infiltrating mucosal and/or skin lesions, showing their pathogenic role in OLP.

Example 13. Patients

Ten patients with OLP treated with ECP were enrolled. They consisted of 8 women and 2 men (mean age: 56.5 years (range: 25-78)). Characteristics of these patients are shown in FIG. 6. Previous treatment with glucocorticoids and immunosuppressive agents was stopped at least 4 weeks before ECP initiation. All patients reached remission under ECP, either complete (CR) or partial (PR, defined by regression of lesions of at least 50%). The patient clinical status was determined at the time of collection of blood sample, which was stored for further analysis.

Example 14. Preparation of Peripheral Blood Mononuclear Cells

Blood was collected at baseline before any ECP treatment ('flare') and at several time points. PBMCs were prepared by Ficoll-Hypaque density gradient centrifugation, and cryopreserved in liquid nitrogen in 8% dimethylsulfoxide, 42% fetal calf serum, and 50% RPMI-1640 medium (Invitrogen). In the experiments assessing the priming of apoptosis of T cells following ECP, PBMC were isolated from fresh blood and treated as described below.

Example 15. Assessment by Flow Cytometry of a Cytotoxic Phenotype

Anti-CD3 FITC (Clone BW264/56, Miltenyi Biotec), anti-CD8-APC (SK1, BD Pharmingen), Dextramer-HPV $E7_{11-20}$-PE (Dext-HPV PE; HLA-A*0201; YMLDLQPETT, Immudex), Dextramer-HIV-1 P17 Gag 77-85-PE (Dext-HIV-PE; HLA-A*0201; SLYNTVATL, Immudex), anti-TCR-Vß3-FITC (JOVI-3, Ancell) were used. Cells were incubated with dextramer for 10 min at room temperature, then anti-CD3, -CD8, -Vß3 antibodies were added for 30 min at 4° C. Perforin and granzyme intracellular staining was performed with specific antibodies in PBS/0.5% BSA/0.1% NaN3 containing saponin (0.5%) at room temperature for 20 min. Stained cells were washed with PBS/0.5% BSA/0.1% NaN3 and analyzed using a FACSCalibur flow cytometer (Becton Dickinson).

Example 16. Assessment with 7-AAD (7-Amino-Actinomycin D) of Priming for Apoptosis Apoptosis was determined using the 7-AAD assay, following the method that we previously reported (Lecoeur, Melki, Saïdi, Gougeon. Methods Enzymol. 2008; 442:51-82). Briefly, PBMCs were stained with 20 µg/ml of the nuclear dye 7-AAD (Sigma-Aldrich) (30 min at 4° C.) for apoptotic cell detection, either directly after their isolation from fresh blood or following 4 days of culture without stimulation. Cells were costained with anti-CD3, CD8, -Vß3 antibodies, washed in PBS/1% BSA/0.1% NaN3 (PBA) and fixed in PBA 1% PFA. Stained samples were acquired on a Cyan™ ADP flow cytometer using Summit software (Beckman Coulter), and analyzed using FlowJo Software. Unlike living cells, apoptotic cells incorporate 7-AAD in their nucleus because of increased membrane permeability, an early feature of apoptosis.

Figure 7:
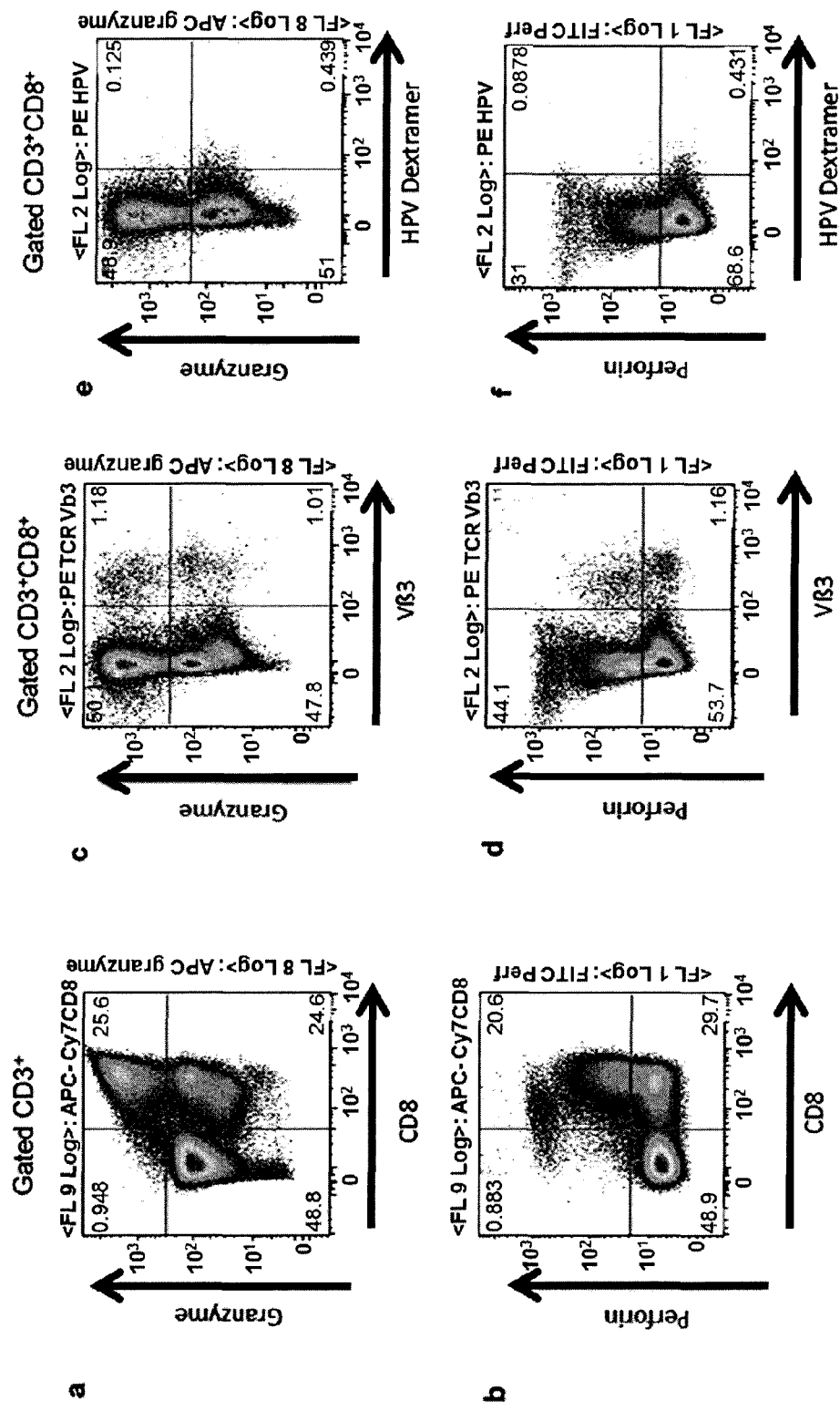
FIGS. 7a-f depict representative dot plots for intracellular perforin and granzyme expression in peripheral lymphocytes from an OLP patient. PBMC from an OLP patient were stained with indicated antibodies according to the method described in the Examples. Analysis of indicated subsets was performed with FlowJo software.

Example 17. Expression of Cytotoxic Granules in Peripheral CD8+Vß3+Dext-HPV+ T Cells from OLP Patients In order to address the hypothesis assuming that clonotypic HPV16-specific CD8+Vß3+ T cells, found in skin lesions, were contributing to the autoimmune destruction of keratinocytes, we assessed the cytotoxic status of these cells. PBMC from four OLP patients were tested for intracellular expression of perforin and granzyme combined to the detection of the markers characterizing the expanded CD8 T-cell subset (CD8, Vß3, HPV-16 dextramer). The staining of PBMC was performed as indicated in Examples 15 and 16. FIG. 7 shows representative dot plots. Data in FIG. 8 summarizes the data obtained in 4 OLP patients. The expression of perforin and granzyme cytotoxic granules by total CD8 T cells was variable, ranging from less than 1% to 22%. CD8+Vß3+ cells also expressed these granules of cytotoxicity in similar proportions, as well as the expanded oligoclonal HPV-specific subset. It is noteworthy that, in each patient tested, granzyme expression was higher than perforin expression, whatever the CD8 subset analyzed, and T cells from patient WO did not express perforin while they significantly expressed granzyme. Altogether these data are compatible with the expression of a cytotoxic activity in HPV-specific CD8+Vß3+ T cells.

Figure 9:
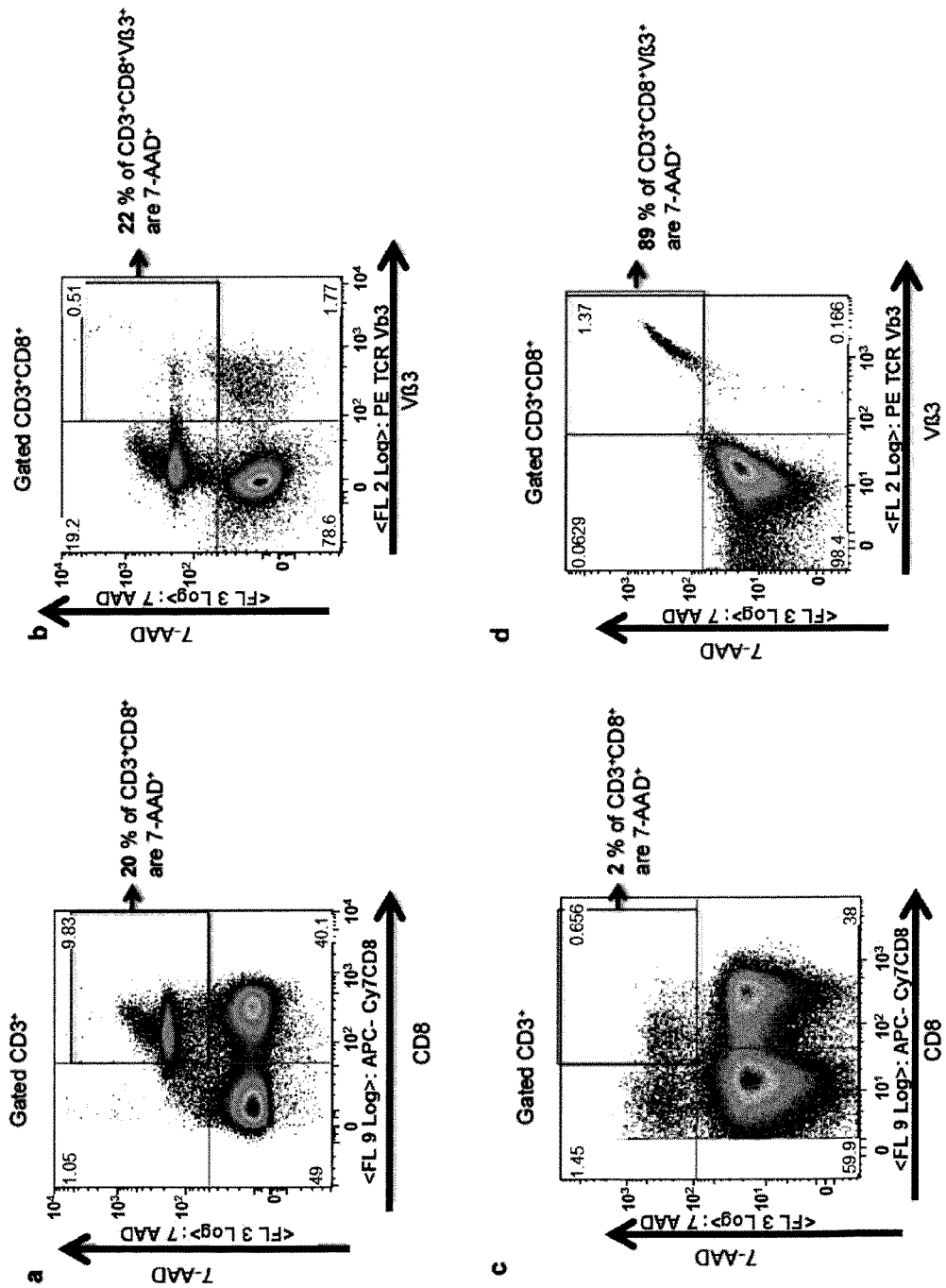
FIGS. 9 a-d depict Priming for apoptosis of CD3+CD8+ Vβ3+ T cells from an OLP patient following ECP. Freshly isolated PBMCs from patient BRE were tested after 3 cycles of ECP. Priming for apoptosis of freshly isolated PBMCs (a and b) and 4-day cultured PBMCs (c and d) was compared using the 7-AAD dye. After short-term culture, the great majority of CD3+CD8+V3+ T cells died of apoptosis (89% were 7-AAD+) in contrast to the whole CD3+CD8+ population (2%).

Example 18. Remission Following ECP is Associated with the Priming for Apoptosis of CD8+Vß3+ T Cells ECP is generally associated with partial or complete remission in patients with OLP. Our study suggests that OLP is associated with the infiltration in lesions of CD3+CD8+V3+ T cells with autoimmune cytotoxic activity, thus destroying the keratinocytes. We addressed the hypothesis that one of the effects of ECP may be the progressive destruction of these CTLs. To do so, we compared the intrinsic fragility of CD3+CD8+V3+ T cells in PBMCs directly after their isolation and after a short-term culture. FIG. 9 shows the data obtained with PBMCs from patient BRE who received 3 cycles of ECP. Ex-vivo, the priming for apoptosis of CD3+CD8+V3+ T cells was similar to that of the whole CD3+CD8+ T cells (around 20%) while, after short-term culture, the great majority of CD3+CD8+V3+ T cells died of apoptosis (89% were 7-AAD+) in contrast to the whole CD3+CD8+ population. Overall these data demonstrate that the CD3+CD8+V3+ subset is primed from premature cell death, and suggest that ECP induced this priming.

The data reported herein demonstrates that a notable proportion of clonal CD8+ blood T-cells of OLP patients are HPV16-specific, they infiltrate mucosal and/or skin lesions, and they decrease or disappear following clinical remission, suggesting their pathogenic role in OLP. The contribution of HPV as an antigenic stimulus of CTL expansion was confirmed by the presence of HPV16 $E7_{11-20}$ specific CD8+ T-cells in the vicinity of dying epithelial cells. These data showing the cytotoxic profile of HPV16-specific CD8 T cells from several OLP patients reinforces the hypothesis of the destruction by these T cells of lesional keratinocytes in OLP patients. Their potential involvement in tissue damage of OLP is also supported by the association between their increased susceptibility to apoptosis and remission after ECP.

We claim:

1. A method for detecting the presence of an immune response against a human papilloma virus infection in a blood sample of an oral lichen planus (OLP) patient, said method comprising:
    isolating T cells from a blood sample from an OLP patient; and
    detecting the presence of an immune response against a human papilloma virus infection in the blood sample by detecting CDR3β length distribution profiles of the TCRVβ3 gene segment in the CD8+ T cells expressing a TCRVβ3 specific for HPV16.

2. The method of claim 1, further comprising treating the patient with an anti-HPV treatment or anti-HPV drug.

3. The method of claim 2, wherein the anti-HPV treatment or anti-HPV drug is cidofovir.

4. The method of claim 1, further comprising preparing nucleic acids from the blood sample and contacting the nucleic acids with an HPV specific primer or probe.

5. A method for detecting the presence of an immune response against a human papilloma virus infection in a blood sample of an oral lichen planus (OLP) patient, said method comprising:
    isolating T cells from the blood sample; and
    detecting expansion of a clonal population of CD8+ TCRVβ3+ T cells recognizing the HPV16 $_{E711-20}$ epitope in the sample,
    wherein said clonal population has a single CDR3β sequence in the TCRVβ3 gene segment.

6. The method of claim 5, wherein the CDR3β sequence in the TCRVβ3 gene segment in the CD8+ T cells of the cell sample encodes any one of SEQ ID NOs 1-10.

7. The method of claim 5, further comprising treating the patient with an anti-HPV treatment or anti-HPV drug.

8. The method of claim 7, wherein the anti-HPV treatment or anti-HPV drug is cidofovir.

9. The method of claim 5, further comprising preparing nucleic acids from the cell sample and contacting the nucleic acids with an HPV specific primer or probe.

* * * * *